(12) United States Patent
Littman et al.

(10) Patent No.: US 11,918,626 B2
(45) Date of Patent: Mar. 5, 2024

(54) VASOINTESTINAL PEPTIDE RECEPTOR INHIBITORS FOR ENHANCEMENT OF GASTROINTESTINAL HEALTH

(71) Applicant: New York University, New York, NY (US)

(72) Inventors: Dan R. Littman, New York, NY (US); Jhimmy Talbot, New York, NY (US)

( * ) Notice: Subject to any disclaimer, the term of this patent is extended or adjusted under 35 U.S.C. 154(b) by 394 days.

(21) Appl. No.: 16/943,610

(22) Filed: Jul. 30, 2020

(65) Prior Publication Data
US 2021/0030845 A1 Feb. 4, 2021

Related U.S. Application Data

(60) Provisional application No. 62/880,553, filed on Jul. 30, 2019.

(51) Int. Cl.
*A61K 38/22* (2006.01)
*A61K 45/06* (2006.01)

(52) U.S. Cl.
CPC .......... *A61K 38/2278* (2013.01); *A61K 45/06* (2013.01)

(58) Field of Classification Search
CPC .......................... A61K 38/2278; A61K 45/06
See application file for complete search history.

(56) References Cited

U.S. PATENT DOCUMENTS 6,911,430 B2 * 6/2005 Gandhi ............. A61K 38/25
424/185.1
9,458,217 B2 * 10/2016 Waller ................. A61N 5/10

OTHER PUBLICATIONS

Baumgart and Sandborn, Crohn's disease, 2012, Lancet, vol. 380, pp. 1590-1605 (Year: 2012).*
Sartor, Reviews in Basic and Clinical Gastroenterology, 2008, Gastroenterology, vol. 134, pp. 577-594 (Year: 2008).*
Festi et al., Gut microbiota and metabolic syndrome, 2014, World Journal of Gastroenterology, vol. 20, Issue 43, pp. 16079-16094 (Year: 2014).*
Tottey et al., Colonic Transit Time is a Driven Force of the Gut Microbiota Composition and Metabolism: In Vitro Evidence, 2017, Journal of Neurogastroenterology and Motility, vol. 23, Issue 1, pp. 124-134 (Year: 2017).*
Vu et al., Inhibition of Vasoactive Intestinal Polypeptide (VIP) Induces Resistance to Dextran Sodium Sulfate (DSS)-Induced Colitis in Mice, 2014, Journal of Molecular Neuroscience, vol. 52, Issue 1, pp. 37-47 (Year: 2014).*
Baumgart et al., Crohn's disease, 2012, Lancet, vol. 380, pp. 1590-1605 (Year: 2012).*
Ma et al., Stone Ileus: An Unusual Presentation of Crohn's Disease, 2016, International Journal of Surgery Research and Practice, vol. 3, Issue 2, pp. 1-3 (Year: 2016).*
Reed et al., Ileus and Small Bowel Obstruction, 2017, Decision Support in Medicine (Year: 2017).*
Dai et al., Increased incidence of prolonged ileus after colectomy for inflammatory bowel diseases under ERAS protocol: a cohort analysis, 2017, Journal of Surgical Research, vol. 212, pp. 86-93 (Year: 2017).*
Vu et al., Inhibition of Vasoactive Intestinal Polypeptide (VIP) Induces Resistance to Dextran Sodium Sulfate (DSS)-Induced Colitis in Mice, 2014, Journal of Molecular Neuroscience, vol. 52, Issue 1, pp. 1-20 (Year: 2014).*

* cited by examiner

*Primary Examiner* — Adam Weidner
*Assistant Examiner* — Brittney E Donoghue
(74) *Attorney, Agent, or Firm* — Hodgson Russ LLP

(57) ABSTRACT

Provided are compositions and methods for maintaining intestinal immune homeostasis. The method comprises administering to an individual an effective amount of a VIPR2 inhibitor. The method may modulate gut resident $CCR6^+$ ILC3 cell function.

3 Claims, 21 Drawing Sheets
(20 of 21 Drawing Sheet(s) Filed in Color)
Specification includes a Sequence Listing.

a

Substance P
Ror(γt)-GFP
β-III-Tubulin b

Tyrosine hyrodxylase
Ror(γt)-GFP
β-III-Tubulin

VASOINTESTINAL PEPTIDE RECEPTOR INHIBITORS FOR ENHANCEMENT OF GASTROINTESTINAL HEALTH

CROSS-REFERENCE TO RELATED APPLICATIONS

This application claims priority to U.S. provisional patent application No. 62/880,553, filed on Jul. 30, 2019, the disclosure of which is incorporated herein by reference.

STATEMENT REGARDING FEDERALLY SPONSORED RESEARCH

This invention was made with government support under grant no. R01 DK103358 awarded by the National Institutes of Health. The government has certain rights in the invention.

BACKGROUND OF THE INVENTION

The intestinal mucosa serves as both a conduit for uptake of food-derived nutrients and microbiome-derived metabolites and as a barrier that prevents tissue invasion by microbes and tempers inflammatory responses to the myriad contents of the lumen. How the intestine coordinates physiological and immune responses to food consumption to optimize nutrient uptake while maintaining barrier functions remains unclear. Disruption of these functions have been implicated in many diseased conditions. As such, there is a continuing need for identifying modulators of nutrient uptake and intestinal barrier functions.

SUMMARY OF THE DISCLOSURE

This disclosure describes how gut neuronal signal triggered by food intake is integrated with intestinal antimicrobial and metabolic responses controlled by type 3 innate lymphoid cells (ILC3). Food consumption rapidly activates a population of enteric neurons that express vasoactive intestinal peptide (VIP). We observed that projections of VIP-producing enteric neurons (VIPen) in the lamina propria are in close proximity to clusters of ILC3 that selectively express VIP receptor type 2 (VIPR2 or VPAC2). ILC3 production of IL-22, which is up-regulated by commensal microbes such as segmented filamentous bacteria (SFB), is inhibited upon engagement of VIPR2. Therefore, there is a reduction in epithelial cell-derived antimicrobial peptide, but enhanced expression of lipid-binding proteins and transporters. During food consumption, activation of VIPen thus enhances growth of epithelial-associated SFB and increases lipid absorption. Our results reveal a feeding- and circadian-regulated dynamic intestinal neuro-immune circuit that promotes a trade-off between innate immune protection and efficiency of nutrient absorption. As intestinal pathogenic microbes disrupt this neuro-immune inhibitory axis, targeting this pathway can be used for enhancing intestinal barrier function to prevent invasion by enteropathogens.

In an aspect, this disclosure provides a method for maintaining intestinal immune homeostasis by administering to an individual in need of treatment, an effective amount of a VIPR2 inhibitor. In an embodiment, the method provides a method for modulating gut resident CCR6$^+$ ILC3 cell function in an individual comprising administering to the individual a composition comprising an effective amount of an inhibitor of VIPR2 expression or function.

BRIEF DESCRIPTION OF THE FIGURES

The patent or application file contains at least one drawing executed in color. Copies of this patent or patent application publication with color drawing(s) will be provided by the Office upon request and payment of the necessary fee.

Vehicle: n=11 (Positive for *C. rodentium*: spleen: 6/11, liver: 8/11), CNO: n=9 (Positive for *C. rodentium*: spleen and liver: 9/9). Data representative of two independent experiments. m, Survival rates for *C. rodentium*-infected Vip$^{IRES-Cre}$ hM3Dq$^{fl-stop-fl/+}$ mice treated with vehicle or CNO (1 mg/Kg, daily, 1-4 d.p.i.: blue rectangle). Vehicle: n=11, CNO: n=11. Data representative of three independent experiments. ****P<0.0001 (Mantel-Cox test). n, o, Bacterial dissemination to the (n) spleen and (o) liver of Vip$^{IRES-Cre}$ hM4Di$^{fl-stop-fl/+}$ mice treated with vehicle or CNO (1 mg/Kg, daily, 1-4 days post-intragastric infection with 4×10$^{10}$ CFU of *C. rodentium*). Log$_{10}$ CFU at 9 d.p.i. Dotted line: limit of detection. Vehicle: n=8 (Positive for *C. rodentium*: spleen: 8/8, liver: 8/8), CNO: n=7 (Positive for *C. rodentium*: spleen: 1/7, liver: 1/7). *P=0.0006 (spleen) and *P=0.0005 (liver) (Mann-Whitney test). Data representative of two independent experiments.

Figure 3:
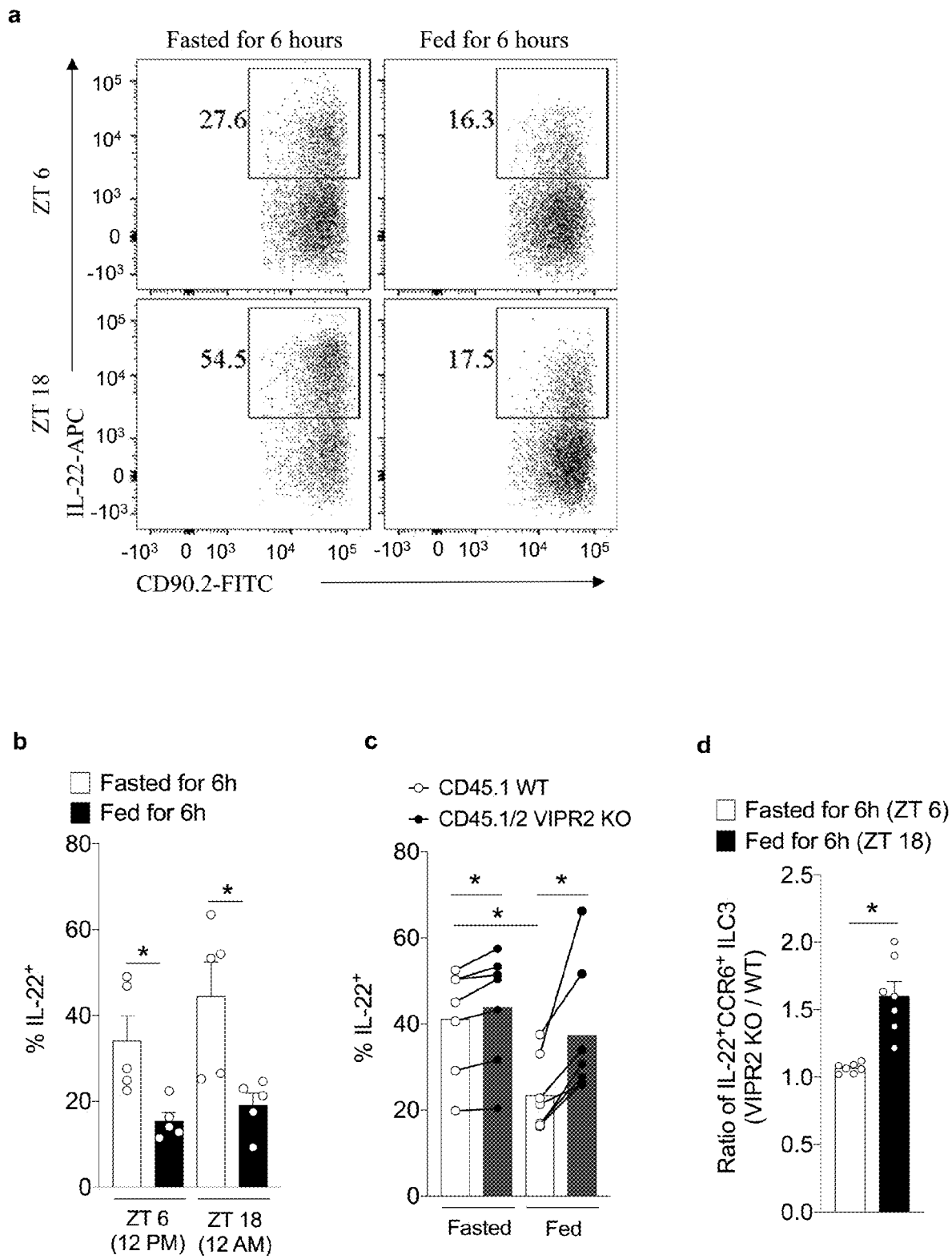
Figure 3:
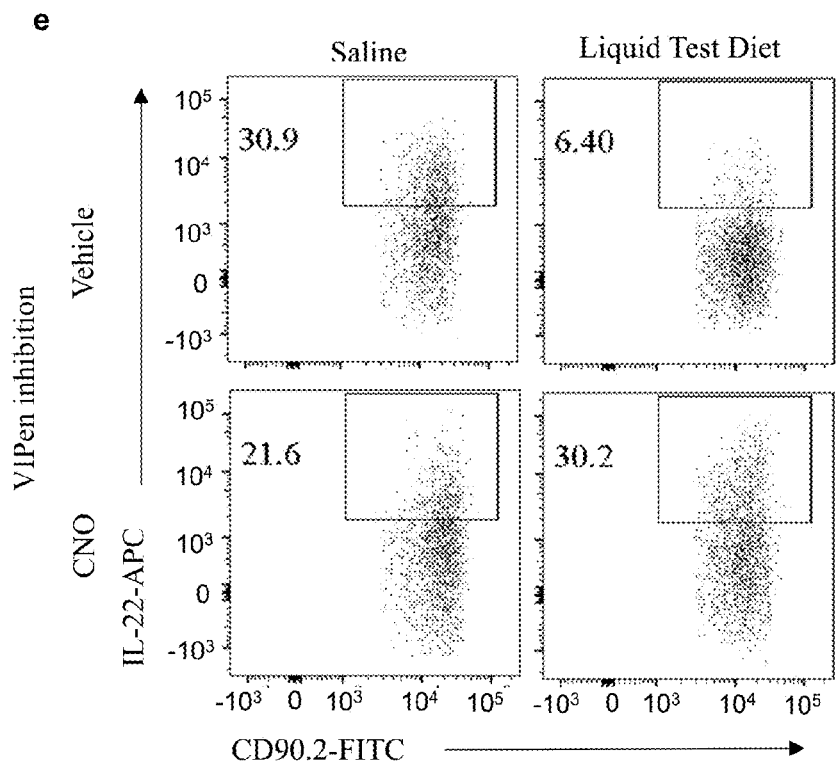
Figure 3:
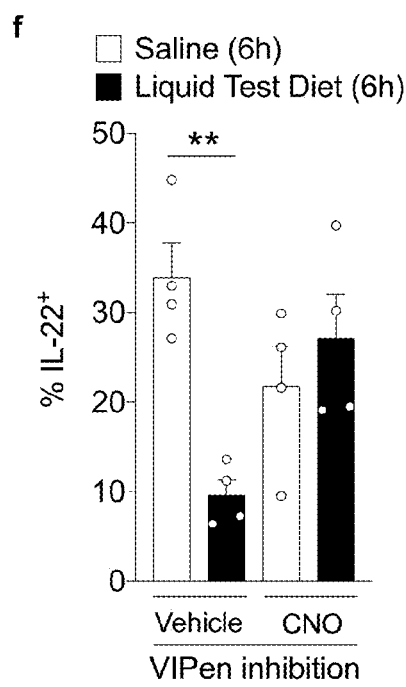

FIG. 3. Feeding reduces IL-22 production by CCR6$^+$ ILC3 through activation of VIPen. a, b, Representative FACS plot (a) and summaries (b) indicating IL-22 expression among CCR6$^+$ ILC3 from the ileum of mice 6 h after feeding or fasting, at ZT6 and ZT18. N=5, *P<0.05 (t-test). Data are representative of two independent experiments. c, IL-22 expression by CCR6$^+$ ILC3 from the ileum of CD45.1 Vipr2$^{+/+}$:CD45.2 Vipr2$^{-/-}$ bone marrow chimeric mice 6 h after fasting (fasted, ZT 6) and 6 h after feeding (fed, ZT 18). n=7, *P<0.05 (paired t-test). Data are representative of two independent experiments. d, Ratio of IL-22-expressing cells, relative to FIG. 3c, among CCR6$^+$ ILC3 from the ileum of CD45.1 Vipr2$^{+/+}$:CD45.2 Vipr2$^{-/-}$ bone marrow chimeric mice 6 h after fasting (Fasted, ZT 6) and 6 hours after feeding (Fed, ZT 18). n=7, *P<0.05 (t-test). e, f, Representative FACS plot (e) and summaries (f) indicating IL-22 expression in CCR6$^+$ ILC3 from the ileum of Vip$^{IRES-Cre}$ hM4Di$^{fl-stop-fl/+}$ mice (DREADD for VIPen inhibition). Mice were treated with vehicle or CNO (1 mg/Kg) and 30 minutes later were fed by intragastric administration of saline (0.4 mL each 45 min, for 6 h) or Liquid Test Diet (500 mg/mL, 0.4 mL each 45 minutes, for 6 h). N=4, **P<0.01 (t-test).

Figure 4:
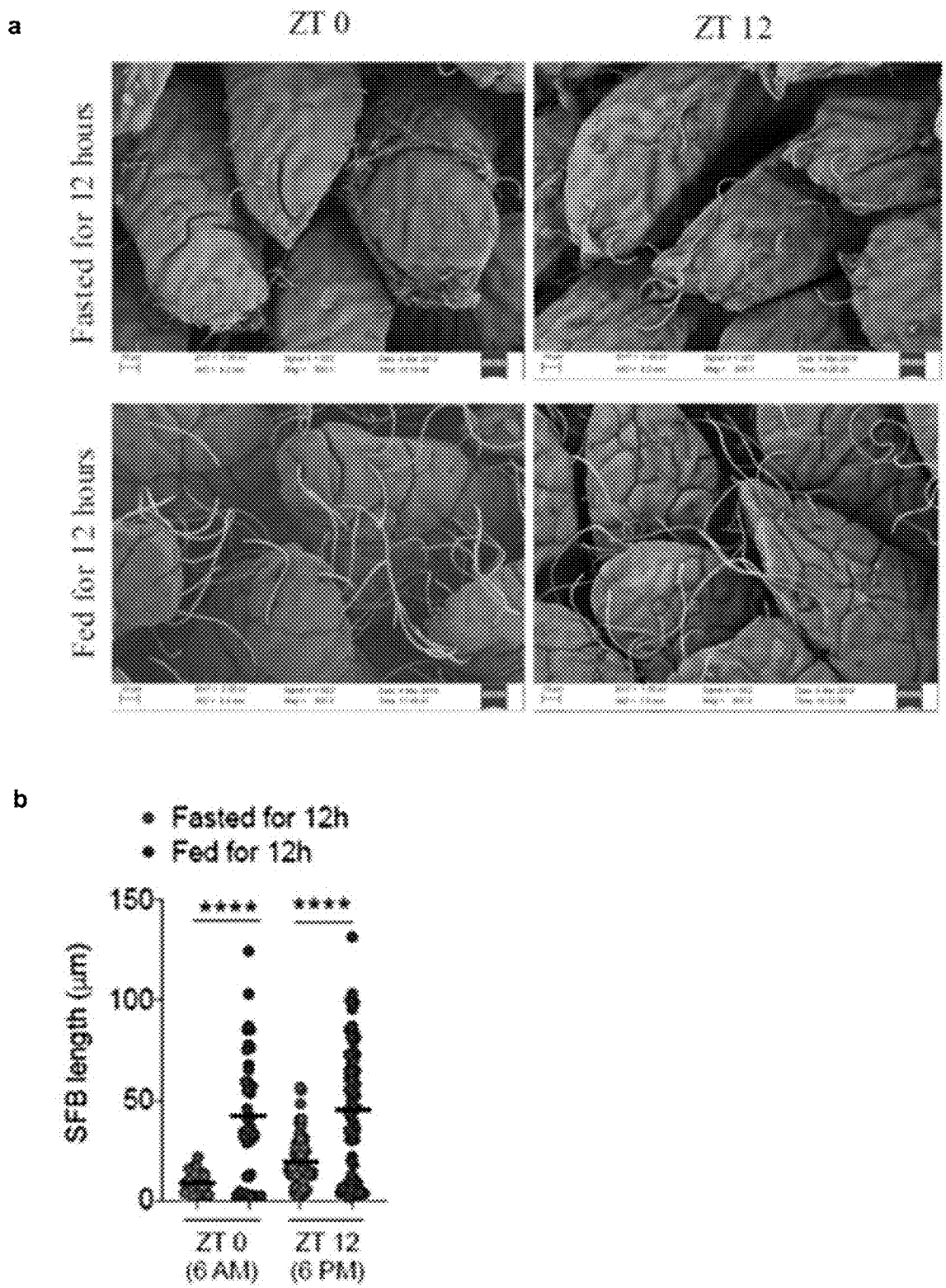
Figure 4:
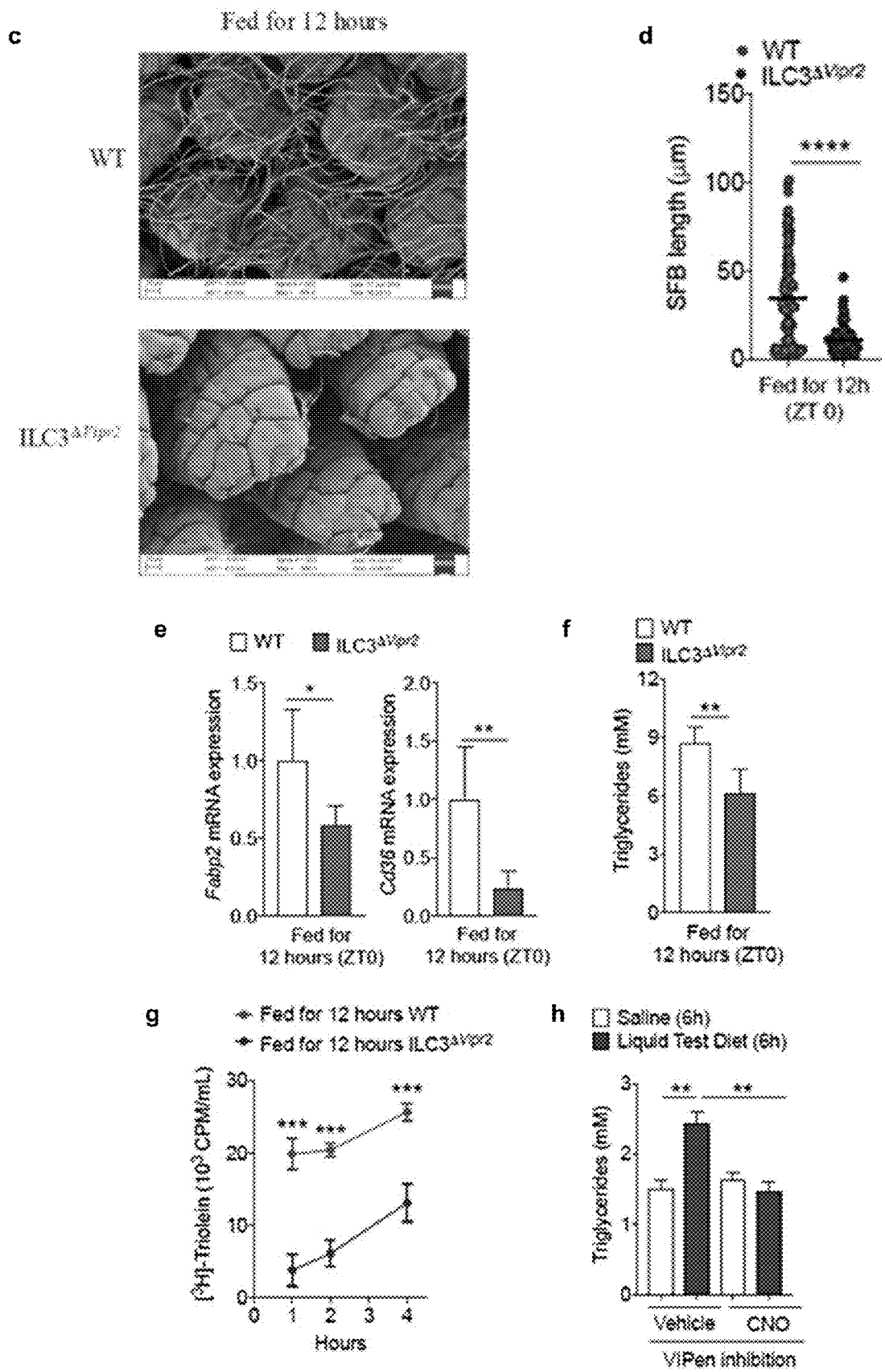

FIG. 4. Dynamic regulation of commensal bacterial growth and lipid absorption by feeding-dependent VIP production. a, b, Representative scanning electron microscopy (SEM) images (a) of epithelium-associated commensal SFB in the ileum of mice 12 h after fasting or feeding at the end of the dark-phase (ZT 0) and the light-phase (ZT 12) and (b) measurements of SFB filament lengths. N=3, **P<0.001 (t-test). c,d, Representative (c) SEM images of epithelium-associated SFB in the ileum of WT and ILC3$^{\Delta Vipr2}$ mice fed for 12 h and (d) measurement of bacterial filament lengths. N=3, **P<0.001 (t-test). e f, Normalized epithelial mRNA expression of Fabp2 and Cd36 (e) and plasma triglyceride content (f) in 12 h fed WT (N=5) and ILC3$^{\Delta Vipr2}$ (N=4) mice. *P<0.05 and P<0.01 (t-test). g, Plasma $^3$H CPM in 12 h fed WT (N=3) and ILC3$^{\Delta Vipr2}$ (N=3) mice after gavage with H-triolein. *P<0.001, (two-way ANOVA). h, Plasma triglyceride content in Vip$^{IRES-Cre}$ hM4Di$^{fl-stop-fl/+}$ mice (DREADD for VIPen inhibition) after gavage with Saline (0.4 mL/each 45 minutes, for 6 hours) or Liquid Test Diet (500 mg/mL, 0.4 mL/each 45 minutes, for 6 hours). Vehicle: N=5, CNO: N=4. **P<0.01, (t-test).

Figure 5:
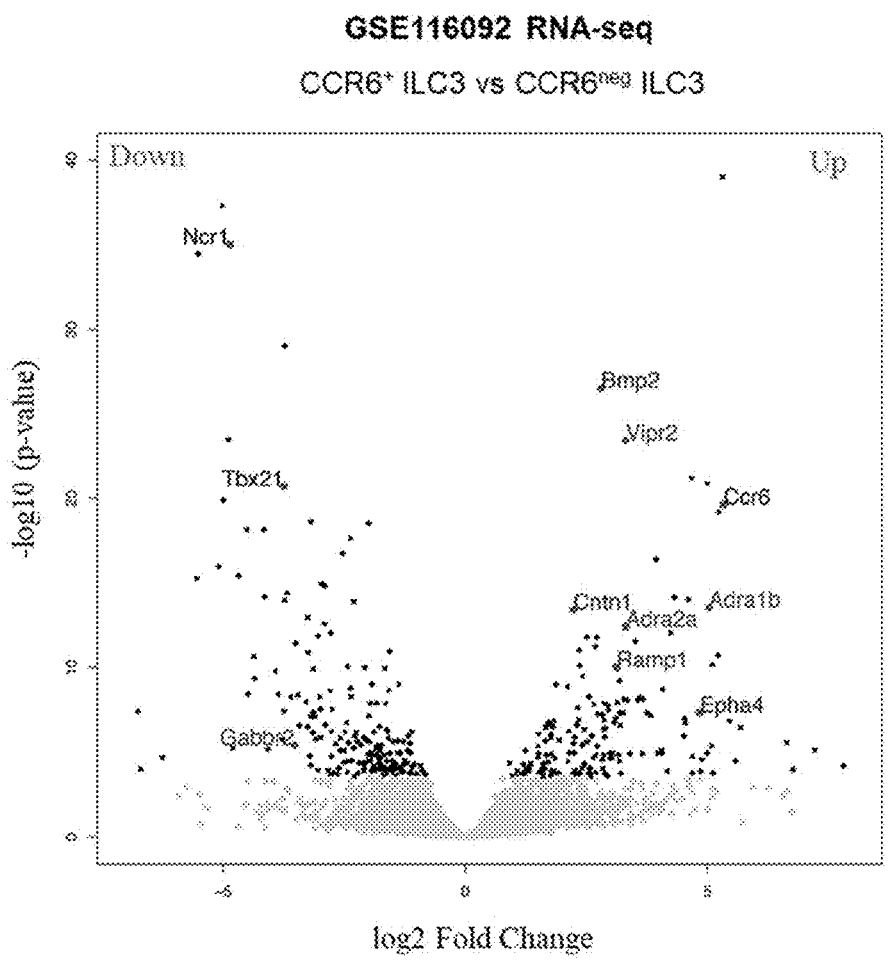
Figure 5:
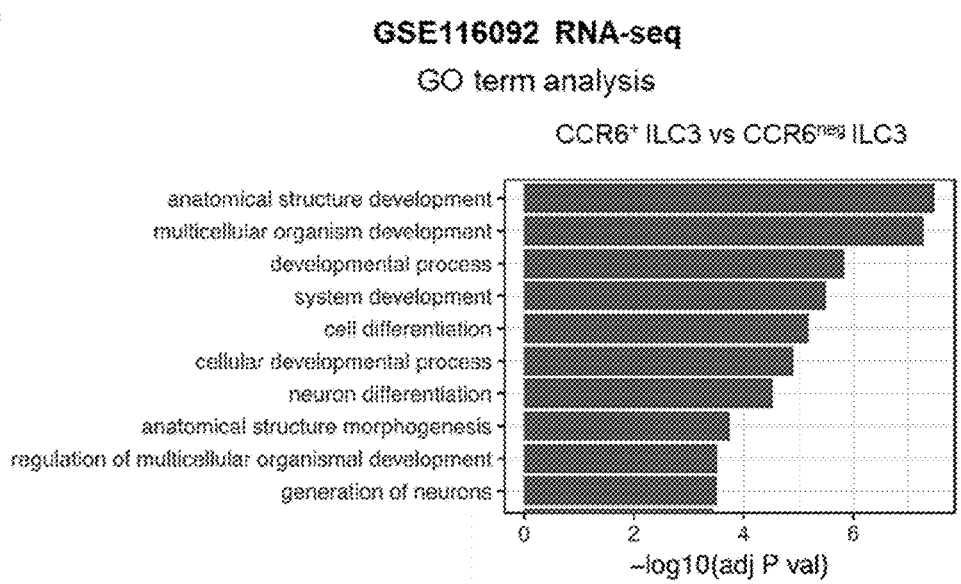
Figure 5:
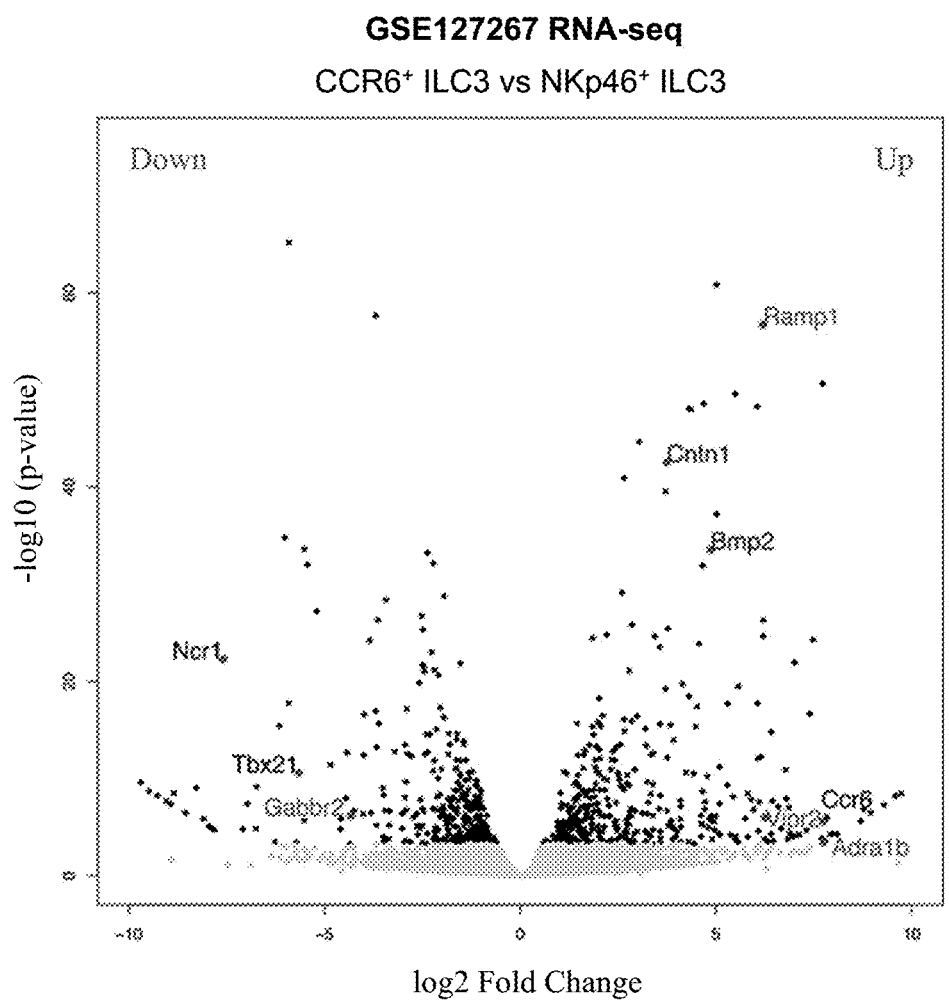

FIG. 5. Enrichment of transcripts related to nervous system/neural functions and development in CCR6$^+$ ILC3. a, Volcano-plot of differentially expressed genes between CCR6$^+$ ILC3 and CCR6$^{neg}$ ILC3 isolated from the small intestine of C57BL/6 mice GSE116092 (Pokrovskii et al., *Immunity.* 2019). Green: Neurotransmitter/neuropeptide receptors, Blue: genes related to nervous system development/axonal guidance and contact. b, Top 10 Gene-Ontology terms from a comparison between subtypes of ILC3 showing enrichment of transcripts related to neuron differentiation and generation in CCR6$^+$ ILC3 when compared to CCR6$^{neg}$ ILC3. Green: Neurotransmitter receptors, Blue: genes related to nervous system development/axonal guidance and contact. c, Volcano-plot of differentially expressed genes between CCR6$^+$ ILC3 (enriched in cryptopatches and ILFs and NKp46$^+$ ILC3 (low presence in CPs and ILFs) (GSE127267 (Heng et al., *Nat Immunol.* 2008; 9(10):1091-1094)).

Figure 6:
Figure 6:
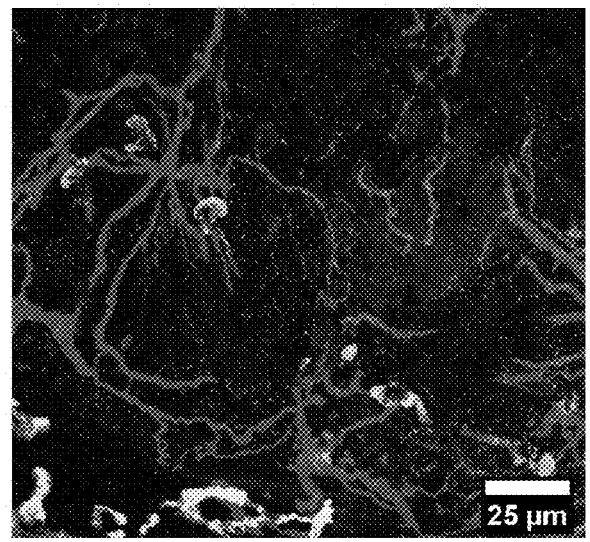
Figure 6:
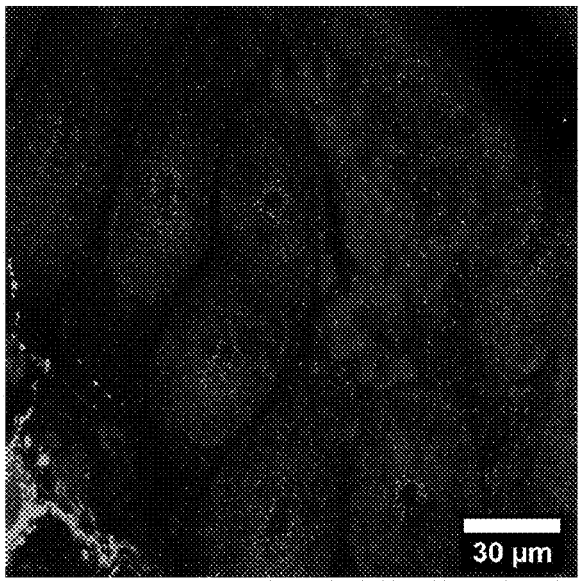
Figure 6:
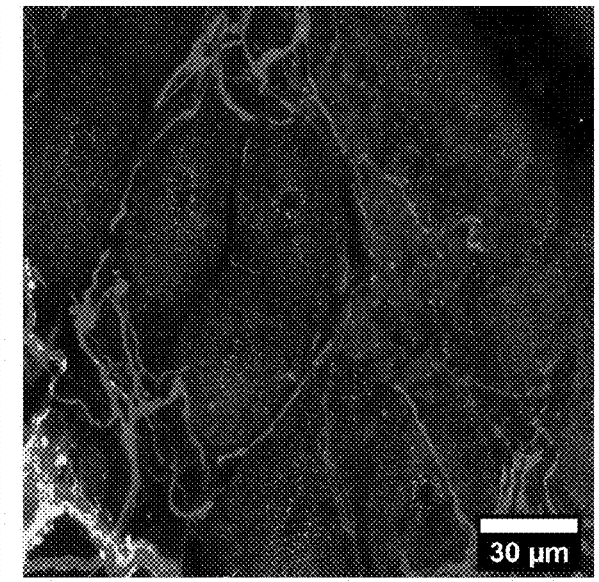
Figure 6:
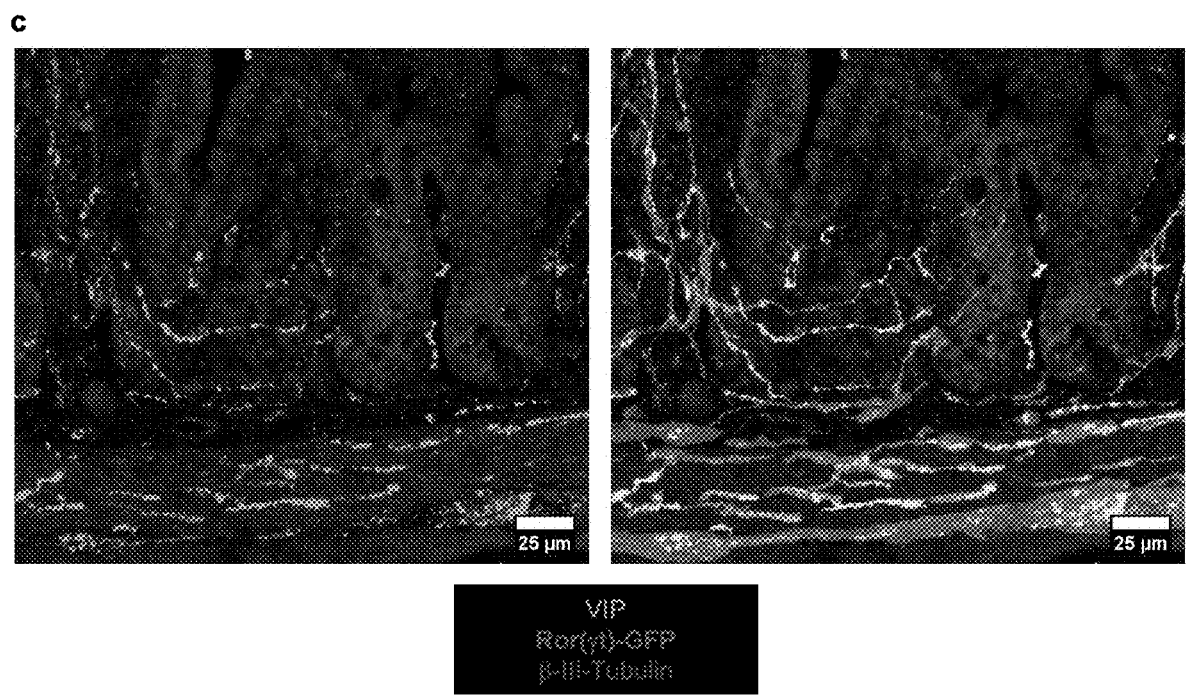

FIG. 6. Neurochemical code of the cryptopatch-associated enteric neurons in the small intestine lamina propria. a-c, Representative immunofluorescence images of different subtypes of lamina propria neuronal projections of enteric neurons in the small intestine of Rorc(γt)$^{EGFP/+}$ mice. (a) Substance P (green) does not represent the neuronal projections (βIII-Tubulin, red) localized inside CPs/ILFs (cluster of GFP$^+$ cells, blue) in the lamina propria. (b) Tyrosine hydroxylase$^+$ neurons (green) are in close proximity but are not the CP-associated neuronal projections (βIII-Tubulin, red) localized inside CPs/ILFs (cluster of GFP$^+$ cells, blue) in the lamina propria. (c) Vasoactive Intestinal Peptide$^+$ (green) neurons (βIII-Tubulin, red) are in close proximity and interacting with ILC3 (GFP$^+$, blue) in CPs/ILFs.

Figure 7:
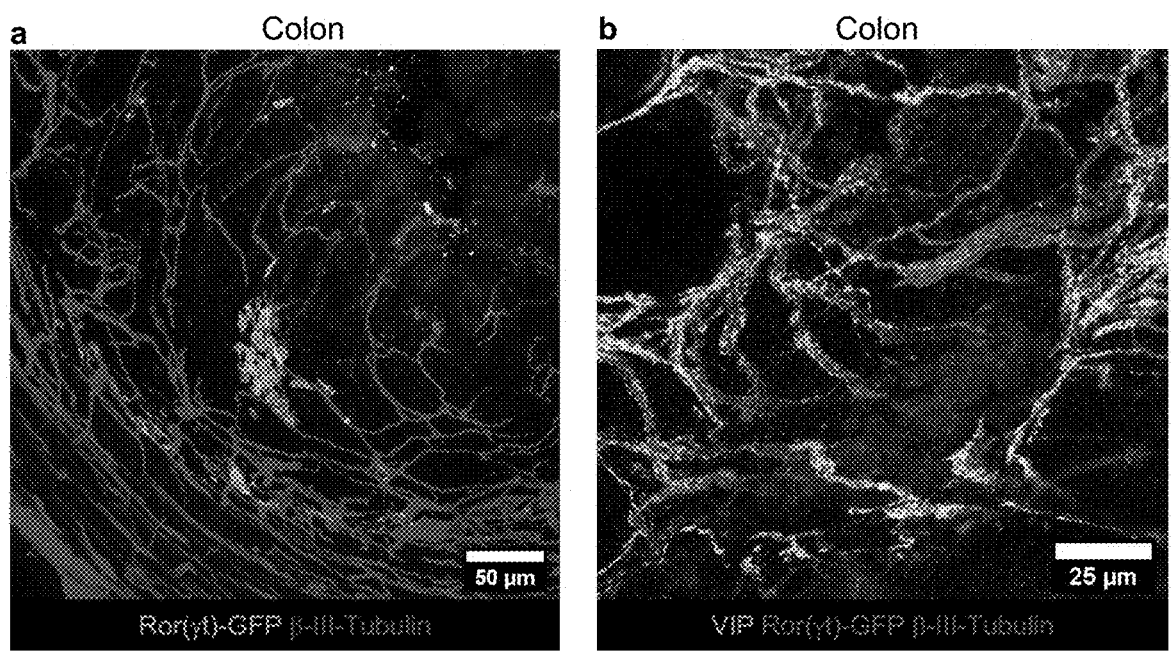

FIG. 7. Cryptopatch-associated enteric neurons are also localized in the large intestine (colon) lamina propria. a, b Representative immunofluorescence images of lamina propria neuronal projections of enteric neurons in the large intestine of Rorc(γt)$^{EGFP/+}$ mice. (a) Cluster of ILC3 (GFP$^+$ cells, green) in close proximity of neuronal projections (βIII-Tubulin, red) of the enteric neurons in the colon lamina propria. (b) Cluster of ILC3 (GFP$^+$ cells, blue) in close proximity of neuronal projections (βIII-Tubulin, red) of the Vasoactive Intestinal Peptide$^+$ enteric neurons (VIPen, green) in the colon lamina propria.

Figure 8:
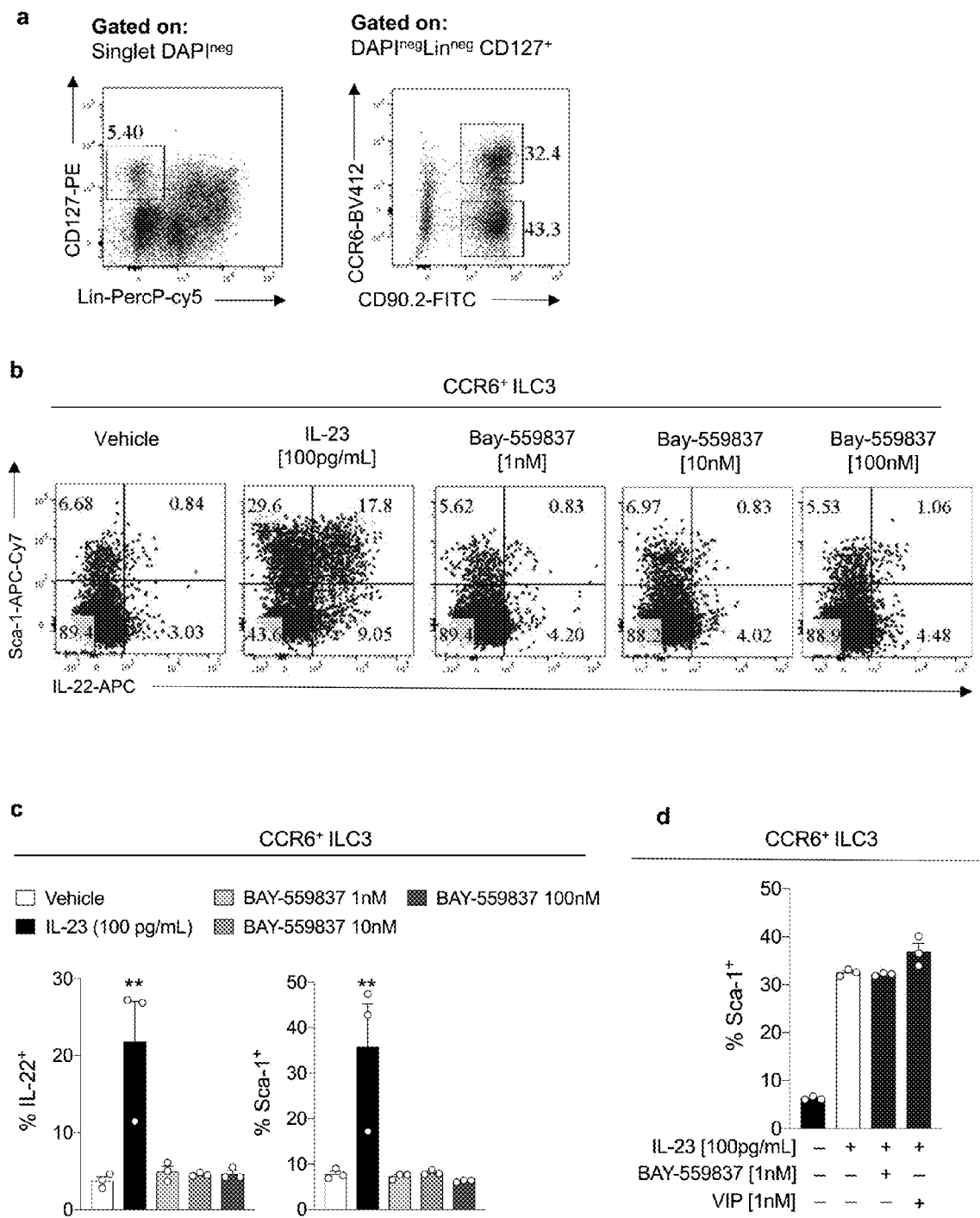
Figure 8:
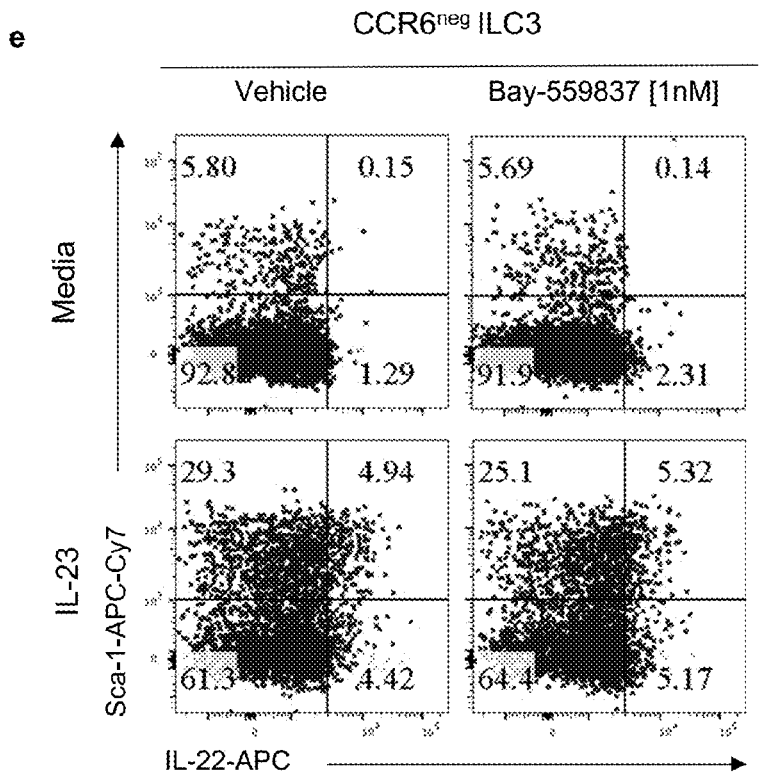
Figure 8:
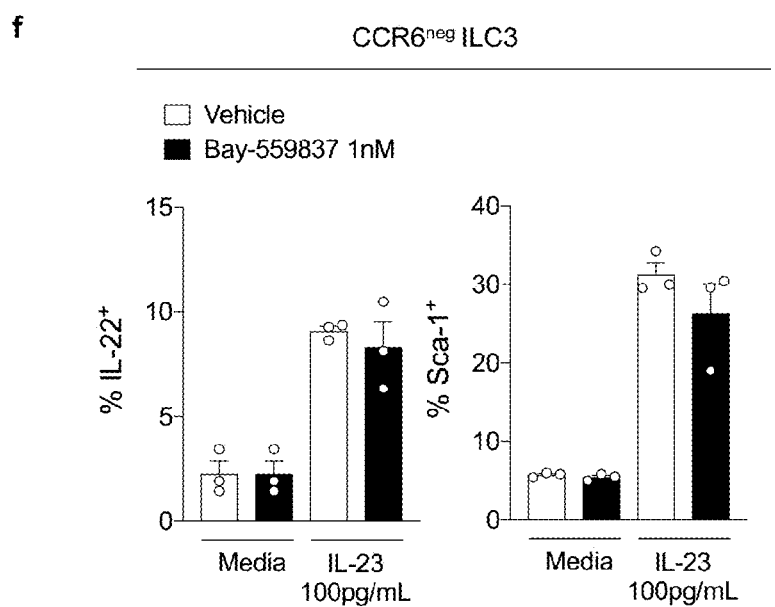

FIG. 8. VIP agonist inhibits in vitro IL-22 production by CCR6$^+$ ILC3. a, FACS plot showing gating strategy for identification and isolation of CCR6$^+$ or CCR6$^{neg}$ ILC3 (DAPI$^{neg}$Lin$^{neg}$ CD127$^+$ CD90.2$^+$). b, c, In vitro activation of VIPR2 alone does not induce cytokine production or activation of CCR6$^+$ ILC3. Representative FACS plots (b) and summary (c) for surface Sca-1 expression and intracellular IL-22 in small intestine lamina propria CCR6$^+$ ILC3 stimulated in vitro for 12 h with IL-23 (100 pg/mL) or different concentrations of the VIPR2 ligand BAY-559837. N=3, **P=<0.01 (One-way ANOVA). Data are representative of two independent experiments. d, In vitro activation of VIPR2 does not modulate IL-23-induced Sca-1 expression on CCR6$^+$ ILC3. Summary of Sca-1 expression in small intestine lamina propria CCR6$^+$ ILC3 stimulated in vitro for 12 h with IL-23 (100 pg/mL) or different concentrations of the VIPR2 ligands BAY-559837 and VIP (N=3). e, f, In vitro VIPR2 activation does not affect IL-23-induced IL-22 production by CCR6$^{neg}$ ILC3. Representative FACS plots (e) and summaries (f) of surface Sca-1 expression and intracellular IL-22 in small intestine lamina propria CCR6$^{neg}$ ILC3 stimulated in vitro for 12 h with IL-23 (100 pg/mL) with/without combination with VIPR2 ligand BAY-559837 (1 nM) (N=3). Data are representative of two independent experiments.

Figure 9:
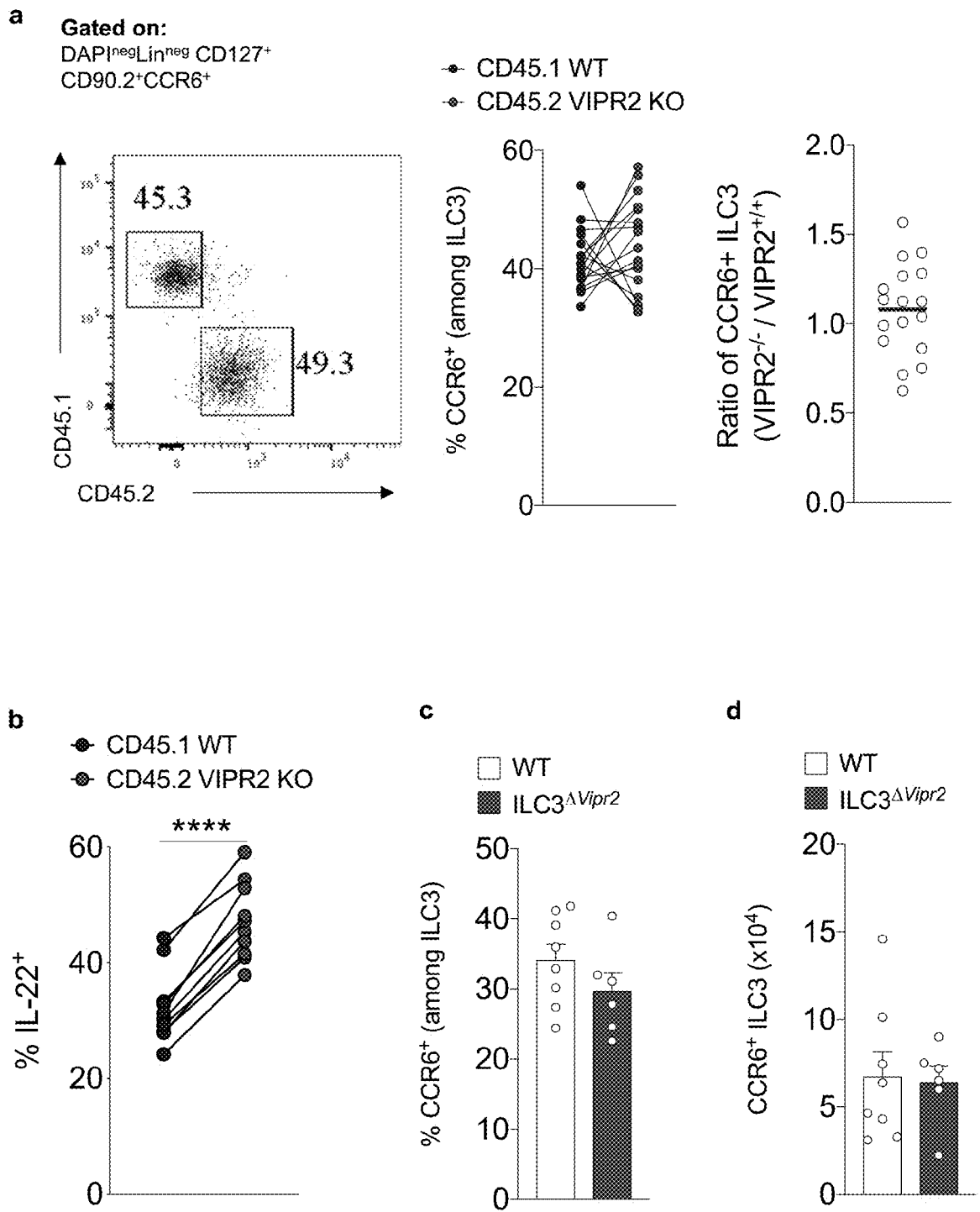
Figure 9:
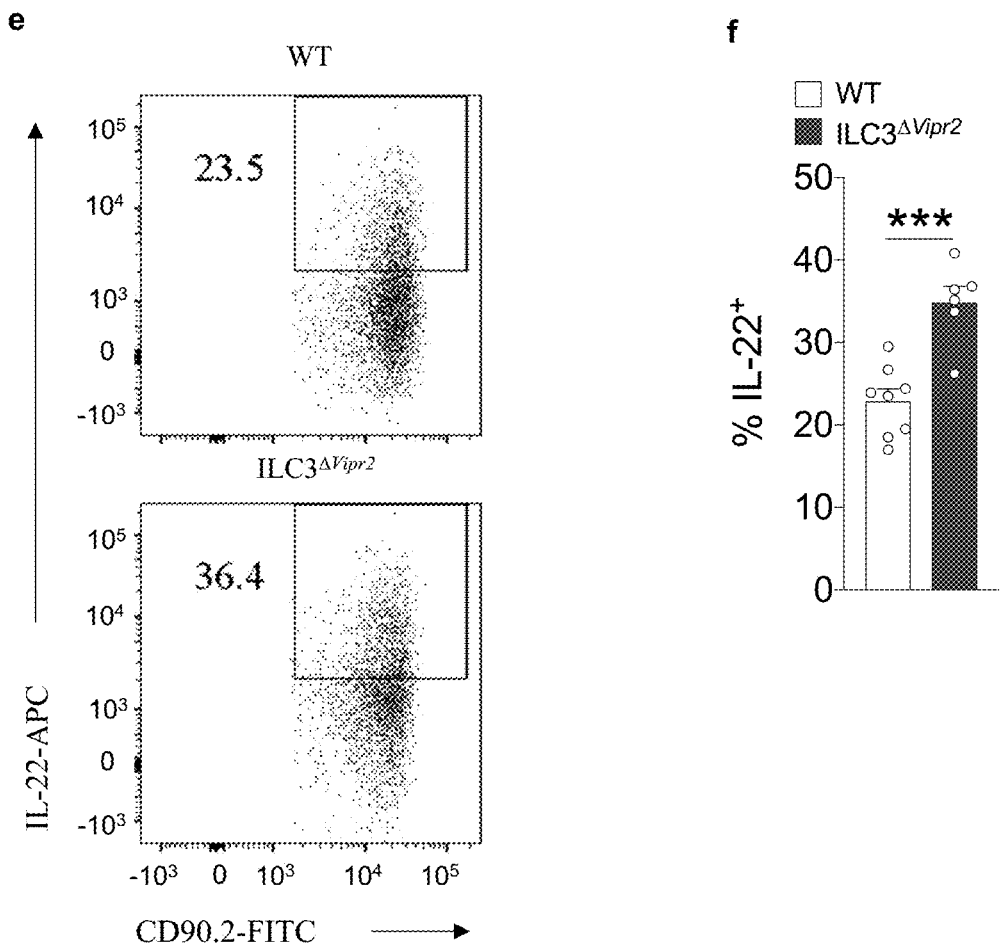

FIG. 9. VIPR2 is required for in vivo inhibition of IL-22 production by CCR6$^+$ ILC3. a, b, Mixed bone marrow chimeras, showing (a) no difference in frequency and ratio of WT (Vipr2$^{+/+}$) vs VIPR2 KO (Vipr2$^{-/-}$) CCR6$^+$ ILC3 in the ileum of mice receiving equal number of cells (N=17 mice, combined from 2 independent experiments) and (b)

VIPR2-dependent inhibition of IL-22 production in WT (Vipr2$^{+/+}$, CD45.1) versus VIPR2 KO (Vipr2$^{-/-}$, CD45.2) CCR6$^+$ ILC3 in the ileum of chimeric mice. N=11, **P<0.0001 (paired t-test). Data are representative of two independent experiments. c, d, Inactivation of Vipr2 in ILC3 (ILC3$^{\Delta Vipr2}$) does not affect (c) frequency or (d) number of CCR6$^+$ ILC3 in the mouse ileum. WT: N=8; ILC3$^{\Delta ILC3}$: N=6. e, f, Representative FACS plot (C) and summaries (D) indicating frequency of IL-22 expression in CCR6$^+$ ILC3 from the ileum of WT and ILC3$^{\Delta Vipr2}$ mice. WT: N=8; ILC3$^{\Delta Vipr2}$: N=6, *P<0.001 (t-test).

Figure 10:
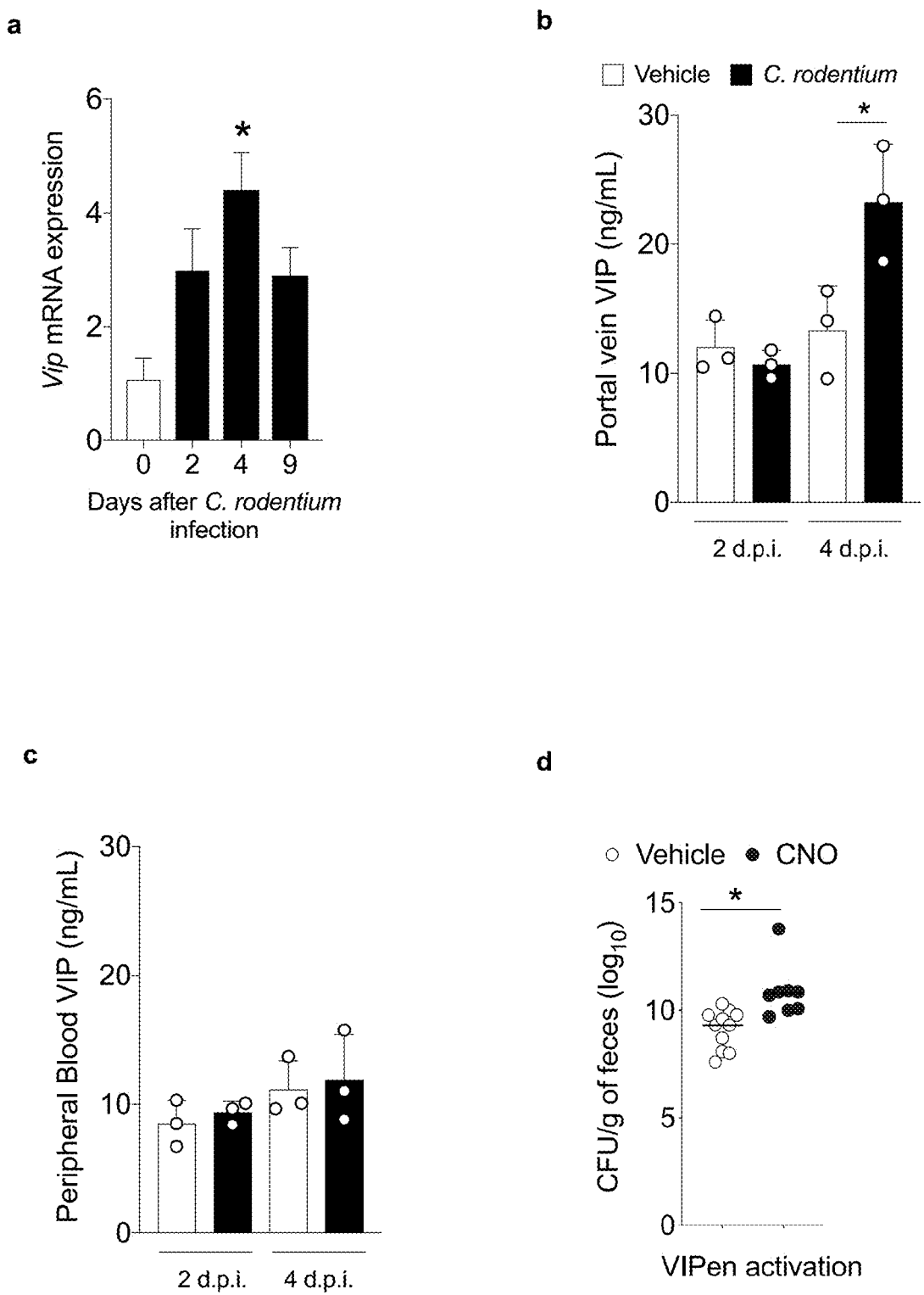
Figure 10:
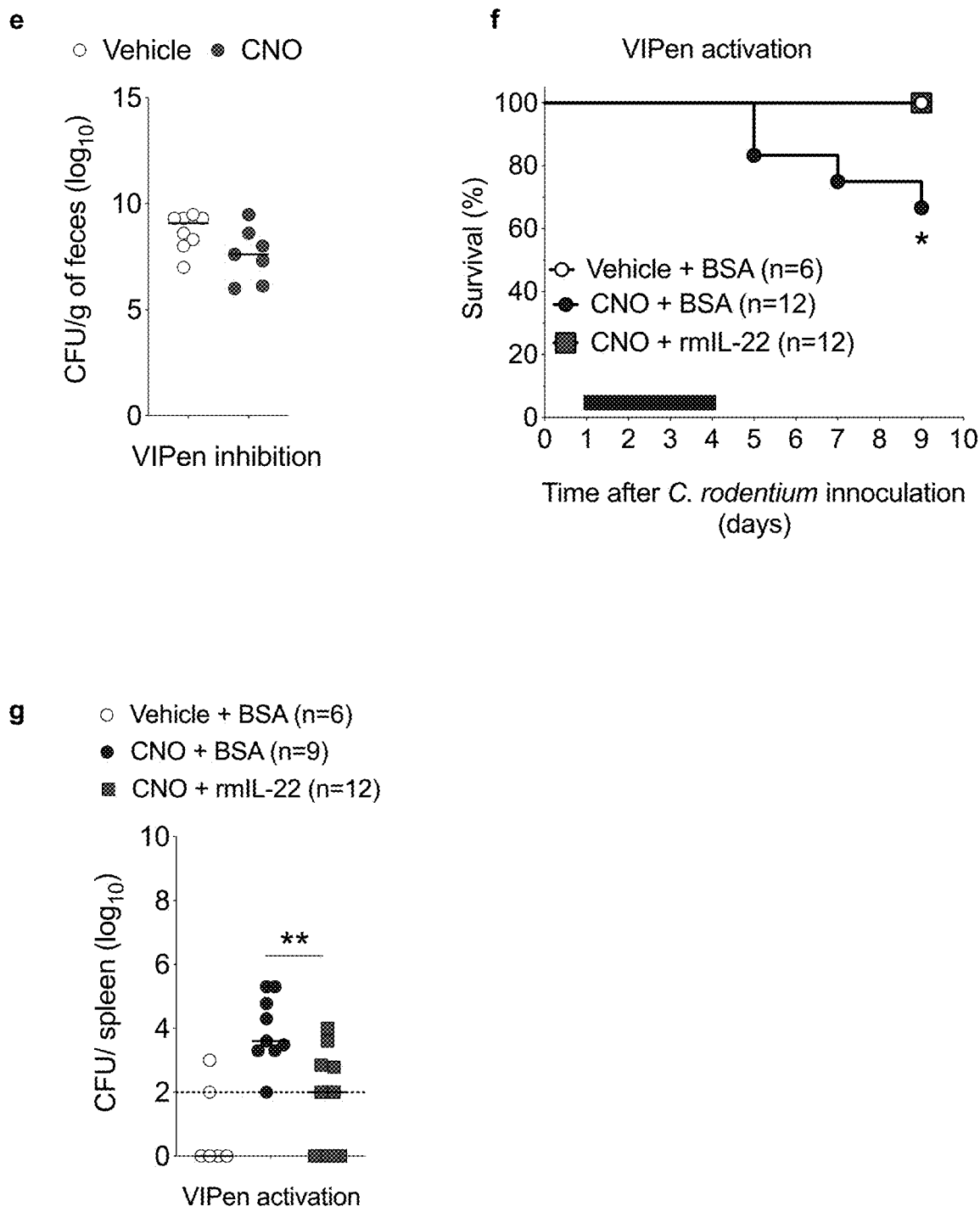

FIG. 10. VIPen regulate host resistance to enteropathogenic *Citrobacter rodentium*. a, Normalized Vip mRNA expression in the large intestine (cecum and proximal colon) of C57BL/6 mice at different time points after oral infection with *Citrobacter rodentium* (2×10$^9$ CFU). Day 0: N=4; Days 2, 4 and 9: N=6. *P<0.05 compared to day 0 (one-way ANOVA). b, c, Increased VIP activity in the gastrointestinal tract but not systemically in mice infected with *C. rodentium*. Concentrations of VIP in plasma from the (b) hepatic portal vein, which drains the gastrointestinal tract, and (c) peripheral blood of mice at different time points after intragastric administration of vehicle or *C. rodentium* (2×10$^9$ CFU). d.p.i: days post-intragastric infection with *C. rodentium*. N=3/group, *P<0.05 (t-test). d, e Infectious burden in feces of (d) Vip$^{IRES-Cre}$hM3Dq$^{fl-stop-fl/+}$ (activating DREADD) and (e) Vip$^{IRES-Cre}$ hM4Di$^{fl-stop-fl/+}$ (inhibitory DREADD) mice treated with vehicle or CNO (1 mg/Kg, daily, 1-4 days post-intragastric infection with 2×10$^9$ CFU for activating and 4×10$^{10}$ CFU for inhibitory DREADD mice). Log$_{10}$ Colony Forming Units (CFU) of *C. rodentium* 9 days post-oral inoculation (9 d.p.i.). Data representative of two independent experiments. Activating DREADD mice: Vehicle: n=11, CNO: n=9. Inhibitory DREADD mice: Vehicle: n=8, CNO: n=7, *P=0.0009 (Mann-Whitney test). f, g, Exogenous treatment with recombinant murine IL-22 (rmIL-22, 250 pg/mouse/day) protects against increase in (f) mortality and (g) bacterial dissemination induced by VIPen activation of Vip$^{IRES-Cre}$ hM3Dq$^{fl-stop-fl/+}$ mice. *P=0.0321 (Mantel Cox test, survival); **P=0.0022 (Mann-Whitney test).

Figure 11:
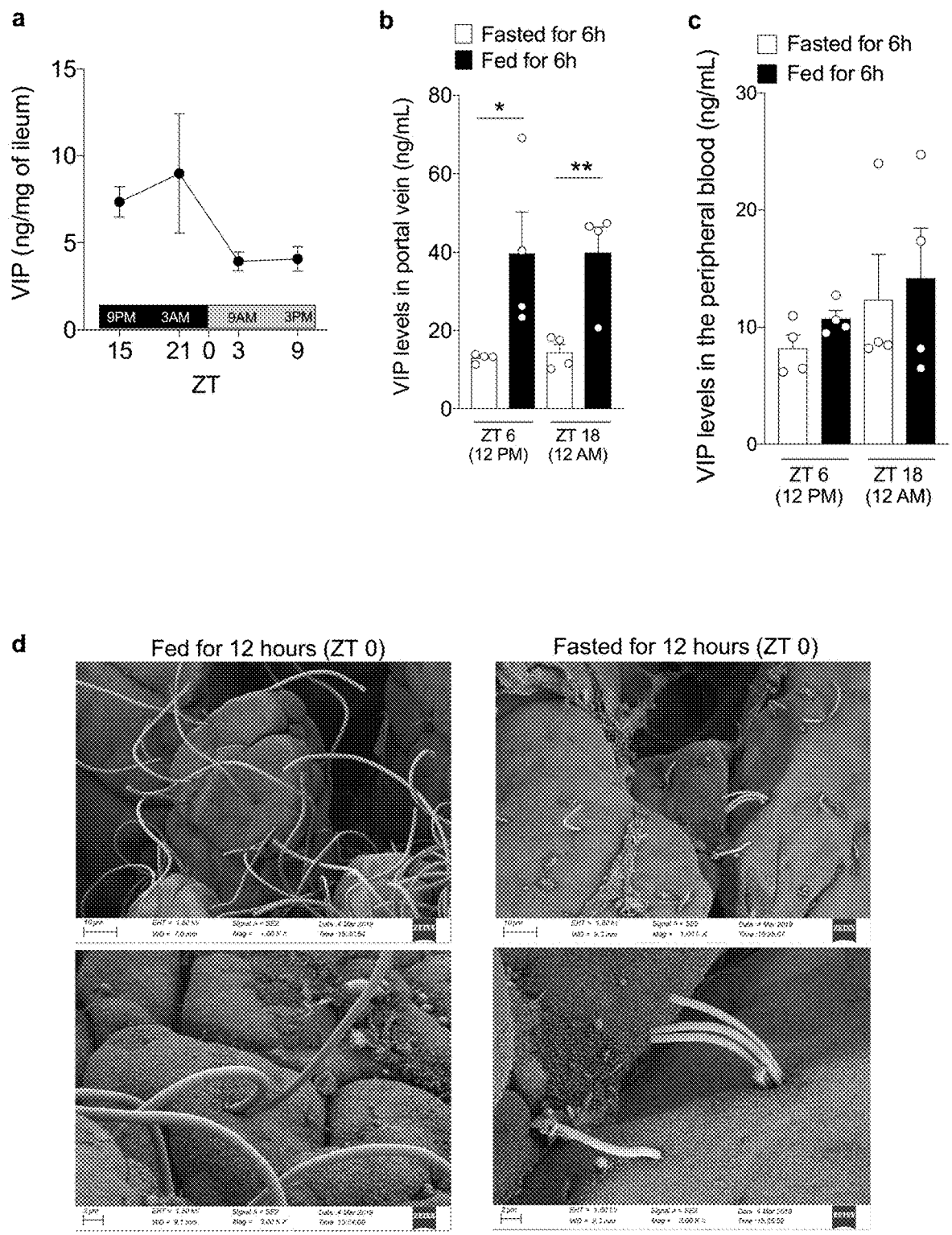
Figure 11:
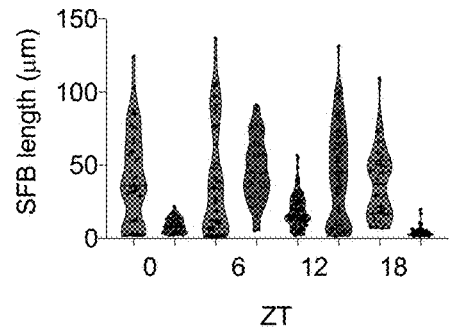
Figure 11:
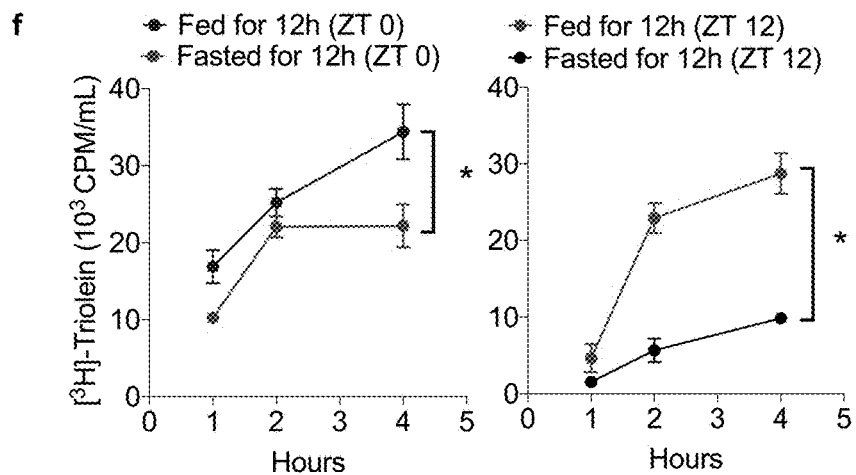
Figure 11:
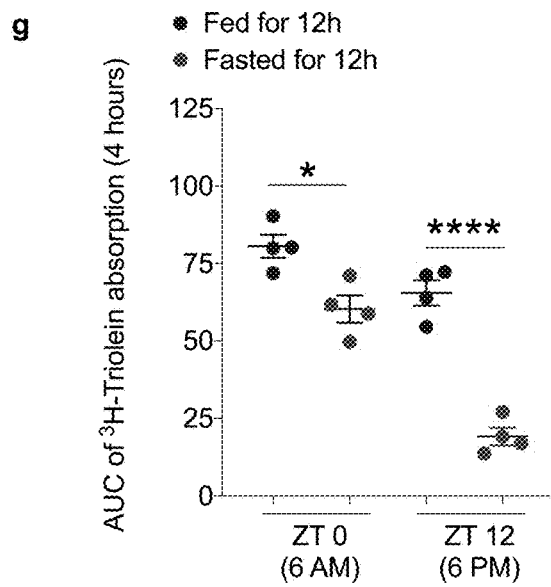

FIG. 11. Feeding controls intestinal VIP release, growth of epithelium-associated segmented filamentous bacteria, and lipid absorption. a, Measurement of concentration of VIP in the ileum reveals higher amounts during dark-phase (feeding period, ZT12-ZT0) than in the light-phase (resting period, ZT0-ZT12). N=4, representative of two independent experiments. b, Concentrations of VIP in plasma isolated from hepatic portal vein blood of mice fed or fasted for 6 h. Blood samples were collected at two different time-points, during the light-phase period (ZT 6, 12 PM) and the dark-phase period (ZT 18, 12 AM). N=4, *P<0.05; **P<0.01 (t-test). c, Concentrations of VIP in plasma isolated from the peripheral blood of mice. Blood samples were collected at two time-points, during the light-phase period (ZT 6, 12 PM) and the dark-phase period (ZT 18, 12 AM). N=4. d, Representative SEM Image (1K and 3K magnification) showing epithelial-attached SFB in the ileum of mice 12 h after feeding (long filaments) or fasting (short-filaments, "stubbles") at ZT 0. e, SFB lengths at different time points during the day in mice that had been fed for two weeks during the dark-phase (ZT12→ZT0) or during the light-phase (ZT0→ZT12). f, g, Plasma $^3$H CPM (counts per minute) in mice fed or fasted for 12 h during the light-phase (ZT 0-ZT 12, red and green circles) or during the dark-phase (ZT 12-ZT 0, blue and black circles) and then gavaged with $^3$H-triolein were sampled at different times (f) and the AUC during 4 h was determined for individual mice from each group (g). AUC: Area under the curve per mL of plasma. N=4 mice per group, *P<0.05 and ****P<0.001 (two-way ANOVA).

DESCRIPTION OF THE DISCLOSURE

This disclosure describes that CCR6$^+$ ILC3 in the intestinal lamina propria are associated with neuronal projections from the enteric nervous system (ENS), which is part of the peripheral autonomic nervous system controlling gastrointestinal functions in response to food intake, microbes, metabolites, etc. We observed that VIPen-derived neuropeptide acts through VIPR2 to inhibit ILC3-mediated innate immune responses. This disclosure provides compositions and methods for inhibiting VIPR2 to maintain or enhance gastrointestinal immune homeostasis and function.

As used herein, the term "treatment" means reduction in one or more symptoms or features associated with the presence of the particular condition being treated. Treatment does not necessarily mean complete remission, nor does it preclude recurrence or relapses. Thus treatment includes ameliorating one or more symptoms associated with an indication. Treatment can be effected over a short time period, over a medium time period, or it can be a long-term treatment, for example within the context of a maintenance therapy.

The term "effective amount" in reference to therapy or "therapeutically effective amount" as used herein is the amount sufficient to achieve, in a single or multiple doses, the intended purpose of treatment. The exact amount desired or required will vary depending on the mode of administration, patient specifics and the like. Appropriate effective amounts can be determined by one of ordinary skill in the art (such as a clinician) with the benefit of the present disclosure.

Where a range of values is provided in this disclosure, it should be understood that each intervening value, to the tenth of the unit of the lower limit and any other intervening value in that stated range is encompassed within the range. All narrower ranges within the indicated broad ranges are also included in the disclosure.

As used in this disclosure, the singular forms include the plural forms and vice versa unless the context clearly indicates otherwise.

In an aspect, the present disclosure provides compositions comprising or consisting essentially of or consisting of one or more inhibitors of VIPR2. VIPR2 inhibitors may inhibit the binding of VIP or an agonist to VIPR2.

An inhibitor of VIPR2 may be a peptide or a peptidomimetic molecule. The peptide may comprise natural and canonical amino acids, non-canonical amino acids or amino acid-like molecules (e.g., peptide-nucleic acid monomers, peptoid monomers and β-amino acids). Examples of peptide based inhibitors include VIP(6-28) or [D-p-Cl-Phe$^6$,Leu$^{17}$]-VIP, which are commercially available from Tocris biologicals.

An inhibitor of VIPR2 may be a small molecule, such as a small molecule that interferes with the binding of VIP or an agonist to VIPR2.

The term "antibody" (or its plural form) as used herein encompasses whole antibody molecules, full-length immunoglobulin molecules, such as naturally occurring full-length immunoglobulin molecules or full-length immunoglobulin molecules formed by immunoglobulin gene fragment recombinatorial processes, as well as antibody fragments. Antibody fragments can be fragments comprising at least one antibody-antigen binding site. The term "antibody" includes e.g. monoclonal, polyclonal, multispecific (for example bispecific), recombinant, human, chimeric, and humanized antibodies. The term "antibody" also encompasses minibodies, and diabodies, all of which preferably specifically inhibit VIPR2. The term "antibody", also encompasses immunoglobulins produced in vivo, in vitro, such as, for example, by a hybridoma, and produced by synthetic/recombinant means. An antibody may be modified by, for example, acetylation, formylation, amidation, phosphorylation, or polyethylene glycolation (PEGylation), as well as glycosylation. Antigen-binding fragments include, but are not limited to, Fab, F(ab'), F(ab')2, Fv, dAb, Fd, CDR fragments, single-chain antibodies (scFv), bivalent single-chain antibodies, single-chain phage antibodies, diabodies, nanobodies and the like. The fragments of the antibodies may be produced synthetically or by enzymatic or chemical cleavage of intact immunoglobulins or may be genetically engineered by recombinant DNA techniques. These techniques are well known in the art. The antibodies useful for the present method may be obtained from a human or a non-human animal. For example, single domain antibodies or nanobodies produced by camelids can also be used. An antibody useful for the present method can be of any class. For example, an antibody of the present invention can be an antibody isotype IgG1, IgG2, IgG3, IgG4, IgM, IgA, IgD or IgE.

In an embodiment, expression of VIPR2 gene can be down regulated by methods known in the art. For example, RNAi-mediated reduction in VIPR2 mRNA may be carried out. RNAi-based inhibition can be achieved using any suitable RNA polynucleotide that is targeted to VIPR2 mRNA. In embodiments, a single stranded or double stranded RNA, wherein at least one strand is complementary to the target mRNA, can be introduced into the cell to promote RNAi-based degradation of target mRNA. In an embodiment, microRNA (miRNA) targeted to the VIPR2 mRNA can be used. In an embodiment, a ribozyme that can specifically cleave VIPR2 mRNA can be used. In an embodiment, small interfering RNA (siRNA) can be used. siRNA can be introduced directly, for example, as a double stranded siRNA complex, or by using a modified expression vector, such as a lentiviral vector, to produce an shRNA. As is known in the art, shRNAs adopt a typical hairpin secondary structure that contains a paired sense and antisense portion, and a short loop sequence between the paired sense and antisense portions. shRNA is delivered to the cytoplasm where it is processed by DICER into siRNAs. siRNA is recognized by RNA-induced silencing complex (RISC), and once incorporated into RISC, siRNAs facilitate cleavage and degradation of targeted mRNA. Generally, shRNA polynucleotide used to suppress VIPR2 mRNA expression can comprise or consist of between 45-100 nucleotides, inclusive, and including all integers between 45 and 100. For delivering siRNA via shRNA, modified lentiviral vectors can be made and used according to standard techniques. Custom siRNAs or shRNA can be obtained from, for example Thermo-Dharmacon or Cellecta for transient transfection resulting in temporary reduction in the targeted mRNA levels. The lentiviruses are capable of stably and permanently infecting target cells, such as by integrating into a genome of a cell.

In an embodiment, antisense nucleic acid molecules capable of blocking or decreasing the expression of VIPR2 may be used. It is routine to prepare antisense oligonucleotide molecules that will specifically bind a target mRNA without cross-reacting with other polynucleotides. Exemplary sites of targeting include, but are not limited to, the initiation codon, the 5' regulatory regions, the coding sequence and the 3' untranslated region. In some embodiments, the oligonucleotides are about 10 to 100 nucleotides in length, about 15 to 50 nucleotides in length, about 18 to 25 nucleotides in length, or more. The oligonucleotides can comprise backbone modifications such as, for example, phosphorothioate linkages, and 2'-O sugar modifications well known in the art.

In an embodiment, the disclosure includes disrupting the target gene such that VIPR2 mRNA and protein are not expressed. For example, the VIPR2 gene (Genbank ID: 7434, NM_003382.5, NP_003373) can be disrupted by targeted mutagenesis. The sequences and all variants thereof are incorporated herein by reference as of the filing date of this application. In embodiments, targeted mutagenesis can be achieved by, for example, targeting a CRISPR (clustered regularly interspaced short palindromic repeats) site in the target gene. So-called CRISPR systems designed for targeting specific genomic sequences are known in the art and can be adapted to disrupt the target gene for making modified cells encompassed by this disclosure. In general, the CRIPSR system includes one or more expression vectors encoding at least a targeting RNA and a polynucleotide sequence encoding a CRISPR-associated nuclease, such as Cas9, but other Cas nucleases can alternatively be used. CRISPR systems for targeted disruption of mammalian chromosomal sequences are commercially available.

The agents of the present disclosure, or pharmaceutically acceptable salts thereof (such as, but not limited to, hydrochloride), can be provided in pharmaceutical compositions for administration by combining them with any suitable pharmaceutically acceptable carriers, excipients and/or stabilizers. Examples of pharmaceutically acceptable carriers, excipients and stabilizer can be found in *Remington: The Science and Practice of Pharmacy* (2005) 21st Edition, Philadelphia, PA Lippincott Williams & Wilkins. For example, suitable carriers include excipients, or stabilizers which are nontoxic to recipients at the dosages and concentrations employed, and include buffers such as acetate, Tris, phosphate, citrate, and other organic acids; antioxidants including ascorbic acid and methionine; preservatives such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol; amino acids such as glycine, glutamine, asparagine, histidine, arginine, or lysine; monosaccharides, disaccharides, and other carbohydrates including glucose, mannose, or dextrins; chelating agents such as EDTA; tonicifiers such as trehalose and sodium chloride; sugars such as sucrose, mannitol, trehalose or sorbitol; surfactant such as polysorbate; salt-forming counter-ions such as sodium; and/or non-ionic surfactants such as Tween or polyethylene glycol (PEG). The pharmaceutical compositions may comprise other therapeutic agents.

The compositions of the present disclosure may be formulated into a variety of forms and administered using a suitable route. For example, the compositions may be administered orally, rectally, or parenterally. The term "parenteral" as used herein includes subcutaneous, intravenous, intramuscular, or intraperitoneal injection and infusion techniques. In an embodiment, the composition is administered orally such as, for example, in the form of a tablet, capsule, pill, powder, paste, granules, elixir, solution, suspension, dispersion, gel, syrup or any other ingestible form. VIPR2 inhibitors may be delivered via liposomes, microparticles, microcapsules or any other delivery agent. The composition may comprise conventionally acceptable carriers, adjuvants, and vehicles as desired.

Solid dosage forms for oral administration may comprise a soft or hard gelatin and a polymer. Suitable polymers include cellulosic polymers such as hydroxypropyl cellulose, hydroxyethyl cellulose, hydroxypropyl methyl cellulose (HPMC), methyl cellulose, ethyl cellulose, cellulose acetate, cellulose acetate phthalate, cellulose acetate, hydroxypropylmethyl cellulose phthalate, hydroxypropylmethyl cellulose succinate and carboxymethylcellulose; acrylic acid polymers and copolymers, such as those formed from acrylic acid, methacrylic acid, methyl acrylate, ammonio methylacrylate, ethyl acrylate, methyl methacrylate and/or ethyl methacrylate (e.g., those copolymers sold under the trade name "Eudragit"); vinyl polymers and copolymers such as polyvinyl pyrrolidone, polyvinyl acetate, polyvinylacetate phthalate, vinylacetate crotonic acid copolymer, and ethylene-vinyl acetate copolymers; and shellac. The solid dosage forms may also comprise saccharides, polysaccharides, or glycoproteins. Examples include corn starch, wheat starch, potato starch, tapioca starch, cellulose, hemicellulose, dextrans, maltodextrin, cyclodextrins, inulins, pectin, mannans, gum arabic, locust bean gum, mesquite gum, guar gum, gum karaya, gum ghatti, tragacanth gum, funori, carrageenans, agar, alginates, chitosans, or gellan gum. For liquid formulations, a VIPR2 inhibitor and any other solid excipients can be dissolved or suspended in a liquid carrier such as water, vegetable oil, alcohol, polyethylene glycol, propylene glycol or glycerin. Liquid compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol. Liquid pharmaceutical compositions of the present invention may also contain a viscosity enhancing agent to improve the mouth feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum. A liquid composition may also contain a buffer such as gluconic acid, lactic acid, citric acid or acetic acid, sodium gluconate, sodium lactate, sodium citrate or sodium acetate.

The present composition may be incorporated into foods and beverages for oral consumption. The food products or beverages may be for any human including children and infants. The composition may comprise flavoring agents, coloring agents, aromatic agents, or other additives including preservatives, emulsifying agents, suspending agents, diluents, sweeteners, a taste enhancer, and and/or a flavorant.

In an aspect, this disclosure provides a method for modulating gastrointestinal immune function. The method comprises administering to an individual in need of treatment an effective amount of a VIPR2 inhibitor. The VIPR2 inhibitor may be present in a composition with a pharmaceutically acceptable carrier.

In an embodiment, the present disclosure provides a method for modulating gut resident CCR6$^+$ ILC3 cell function in an individual comprising administering to the individual a composition comprising or consisting essentially of an effective amount of an inhibitor of VIPR2. Administration of VIPR2 inhibitor may result in one or more of the following: inhibition of binding of VIP or an agonist to VIPR2, increase in production of IL-22 from CCR6$^+$ ILC3 intestinal cells, decrease in fat absorption by the intestine, strengthening or maintenance of integrity of the intestinal epithelial barrier, increase or maintenance of production of antimicrobial peptides in the intestines, maintenance of the level of gut resident bacteria, decrease of number of pathogenic bacteria in the gut, such as during gastrointestinal infections, and protection of the gut against genotoxic stress (described in Gronke et al., 2019 February; 566(7743):249-253. doi: 10.1038/s41586-019-0899-7).

The present compositions may be useful for maintaining or enhancing the integrity of the intestinal epithelial barrier or reducing the breakdown of the intestinal epithelial barrier during diseased or GI stress conditions. For example, the integrity of the intestinal barrier may be compromised during GI or other infections. An example of a condition wherein the intestinal barrier is considered to break down leading to a condition often referred to as "leaky gut" is HIV infection. Leaky gut may also be associated with persistent inflammation or chronic illnesses including irritable bowel syndrome, celiac disease and diabetes. The method comprises administering to an individual in need of treatment a composition comprising or consisting essentially of an effective amount of a VIPR2 inhibitor.

In an embodiment, the present disclosure provides a method for modulating the intestinal microbiome in an individual comprising administering to an individual in need of treatment a composition comprising or consisting essentially of an effective amount of a VIPR2 inhibitor. The method may be useful for an individual who is suffering from dysbiosis of intestinal microbiome. Dysbiosis of intestinal microbiome may occur in acute or chronic diseased conditions, infections, therapeutic interventions, such as chemotherapy or antimicrobial treatments (including antibiotics).

It has been reported that stroke promotes the translocation and dissemination of certain strains of bacteria that originate in the host gut microbiota. In an embodiment, this disclosure provides a method of reducing stroke associated infections comprising administering to an individual in need of treatment (such as an individual who has had a stroke) a composition comprising or consisting essentially of an effective amount of a VIPR2 inhibitor.

In an embodiment, this disclosure provides a method for maintaining intestinal immune homeostasis in an individual comprising administering to an individual in need of treatment a composition comprising or consisting essentially of an effective amount of a VIPR2 inhibitor. The method may be useful in an individual who is at risk of disrupting or disturbing the intestinal immune homeostasis, such as, for example, an individual who is at risk of an infection, or who is to undergo a therapeutic regimen such as a chemotherapy or radiation treatment. Intestinal homeostasis may comprise not only appropriate microbiota but also the right balance of effector T cells and regulatory T cells, pro- and anti-inflammatory cytokines, and intact barrier functions (i.e., activity of all the other cells/factors on the various epithelial cell components).

In an embodiment, this disclosure provides a method for reducing the severity of metabolic disease in an individual comprising administering to an individual in need of treatment a composition comprising or consisting essentially of an effective amount of a VIPR2 inhibitor. Examples of metabolic diseases include obesity, diabetes, atherosclerosis, hypertriglyceridemia and non-alcoholic steatohepatitis (NASH).

In an embodiment, this disclosure provides a method for reducing the severity of a gastrointestinal disease in an individual comprising administering to an individual in need of treatment a composition comprising or consisting essentially of an effective amount of a VIPR2 inhibitor. Examples of the gastrointestinal diseases include irritable bowel syndrome, inflammatory bowel disease, and celiac disease, and those resulting from acute or chronic microbial infections.

In an embodiment, this disclosure provides a method for protecting against or preventing genotoxic stress to intestinal cells comprising administering to an individual in need of treatment a composition comprising or consisting essentially of an effective amount of a VIPR2 inhibitor. The genotoxic stress may be caused by administration of a therapeutic agent, which may be a chemotherapeutic agent, a diagnostic agent or any other exogenous agent. In an embodiment this disclosure provides a method for maintaining genomic integrity of intestinal cells comprising administering to an individual in need of treatment a composition comprising or consisting essentially of an effective amount of a VIPR2 inhibitor. The intestinal cells may be intestinal epithelial cells.

In an embodiment, this disclosure provides a method for reducing intestinal damage during chemotherapy comprising administering to an individual who is undergoing or who is going to undergo chemotherapy a composition comprising or consisting essentially of an effective amount or a VIPR2 inhibitor. The administration of VIPR2 inhibitor can be carried out concurrently or sequentially with administration of the chemotherapeutic agent. In an embodiment, this disclosure provides a method for treatment of cancer comprising administering to an individual in need of treatment a composition comprising or consisting essentially of chemotherapeutic agent and a VIPR2 inhibitor, wherein the treatment has reduced intestinal toxicity as compared to treatment without the VIPR2 inhibitor. The chemotherapeutic agent and the VIPR2 inhibitor may be administered together or separately, by the same or different routes and over the same period of time or different times.

In an embodiment, this disclosure provides a method for reducing the severity of food allergy in an individual comprising administering to an individual in need of treatment a composition comprising an effective amount of a VIPR2 inhibitor. Examples of food allergies include allergies due to peanuts or gluten or any other food product or food additive.

In an embodiment, this disclosure provides a method for reducing uptake/absorption of fat from the intestine of an individual comprising administering to the individual in need of treatment a composition comprising or consisting essentially of an inhibitor of VIPR2.

In an embodiment, the disclosure provides a method for reducing IL-22 production by gut resident CCR6$^+$ ILC3 cells comprising activating VIPen function and/or VIPR2. VIPen function activation or VIPR2 activation may be carried out by using specific activators of VIPen and/or agonists of VIPR2. This method can be used to modulate nutrient uptake, such as, for example, fat uptake. In an embodiment, this disclosure provides a method for increasing uptake or absorption of lipids or lipophilic materials from the intestine comprising administering to an individual a composition comprising or consisting essentially of an activator of VIPen and/or an agonist of VIPR2. This method may be useful in treatment of malabsorption disorders, such as, for example, cachexia and the like. The method may also be useful in improving absorption of lipophilic therapeutic or diagnostic agents from the intestine. The method may be used for any condition in which an improvement of fat absorption is desired.

The compositions may be introduced as a single administration or as multiple administrations or may be introduced in a continuous manner over a period of time. For example, the administration(s) can be a pre-specified number of administrations or daily, weekly or monthly administrations, which may be continuous or intermittent, as may be clinically needed and/or therapeutically indicated. The VIPR2 inhibitors may alternatively, be added to food products of beverages for easy consumption.

In various embodiments, this disclosure provides:

A method for modulating gut resident CCR6$^+$ ILC3 cell function in an individual comprising administering to the individual a composition comprising an effective amount of an inhibitor of VIPR2 expression or function. The administration of the VIPR2 inhibitor may result in: increasing production of IL-22 from CCR6$^+$ ILC3 cells; decreasing fat absorption by the intestine; strengthening or maintaining the integrity of the intestinal epithelial barrier; increasing or maintaining production of antimicrobial peptides in the intestines; maintaining the level of gut resident bacteria; decreasing the number of pathogenic bacteria; and/or reducing or preventing genotoxic stress.

A method for maintaining or enhancing the integrity of the intestinal epithelial barrier in an individual comprising administering to an individual in need of treatment a composition comprising an effective amount of a VIPR2 inhibitor. The individual is infected with a Human Immunodeficiency Virus.

A method for modulating the intestinal microbiome in an individual comprising administering to an individual in need of treatment a composition comprising an effective amount of a VIPR2 inhibitor.

A method for reducing the severity of metabolic diseases in an individual comprising administering to an individual in need of treatment a composition comprising an effective amount of a VIPR2 inhibitor. The metabolic disease is obesity, diabetes, atherosclerosis, hypertriglyceridemia or non-alcoholic steatohepatitis.

A method for reducing the severity of a gastrointestinal disease in an individual comprising administering to an individual in need of treatment a composition comprising an effective amount of a VIPR2 inhibitor. The gastrointestinal disease may be irritable bowel syndrome, inflammatory bowel disease, or celiac disease. The gastrointestinal disease may be due to acute or chronic microbial infection.

A method for reducing the severity of food allergy in an individual comprising administering to an individual in need of treatment a composition comprising an effective amount of a VIPR2 inhibitor. The food allergy may be due to any allergen in the food, such as, peanut or gluten.

A method for maintaining intestinal immune homeostasis in an individual comprising administering to an individual in need of treatment a composition comprising an effective amount of a VIPR2 inhibitor.

A method for protecting against or preventing genotoxic stress to intestinal cells, or for maintaining genomic integrity of intestinal cells (such as intestinal epithelial cells) comprising administering to an individual in need of treatment a composition comprising an effective amount of a VIPR2 inhibitor. The genotoxic stress may be caused by administration of a therapeutic agent. The therapeutic agent is a chemotherapeutic agent.

A method of treatment of cancer comprising administering to an individual in need of treatment a chemotherapeutic agent in combination with an effective amount of a VIPR2 inhibitor, wherein administration of the VIPR2 inhibitor reduces the genotoxic stress to the intestinal cells of the individual. The chemotherapeutic agent and the VIPR2 inhibitor may be administered sequentially or concurrently.

A method of improving lipid uptake from the intestine comprising administering to an individual a composition comprising an effective amount of an activator of VIPen, and/or an agonist of VIPR2. As a result of the treatment, IL-22 production by gut CCR6$^+$ ILC3 may be decreased. The individual in need of treatment may be afflicted with malabsorption disorder or cachexia.

A method of improving the uptake of lipophilic agents from the intestine comprising administering to an individual a composition comprising an effective amount of an activator of VIPen, and/or an agonist of VIPR2. The lipophilic agent may be a therapeutic agent or a diagnostic agent.

A method of reducing stroke associated infection comprising administering to an individual who has suffered a stroke a composition comprising an effective amount of a VIPR2 inhibitor.

By the methods of the present disclosure, where VIPR2 inhibition is effected, IL-22 production by gut CCR6$^+$ ILC3 may be increased.

The inhibitor of VIPR2 activation may be VIP(6-28) or [D-p-Cl-Phe$^6$,Leu$^7$]-VIP. The inhibitor of VIPR2 may inhibit binding of VIP to VIPR2. VIPR2 inhibitor may be a small molecule, a peptide, an antibody or a fragment thereof. VIPR2 inhibition may be carried out by using CRISPR/cas enzyme, or siRNA or antisense oligonucleotide.

The following examples are provided as illustrative examples and are not intended to be restrictive in any way.

Example

Figure 1:
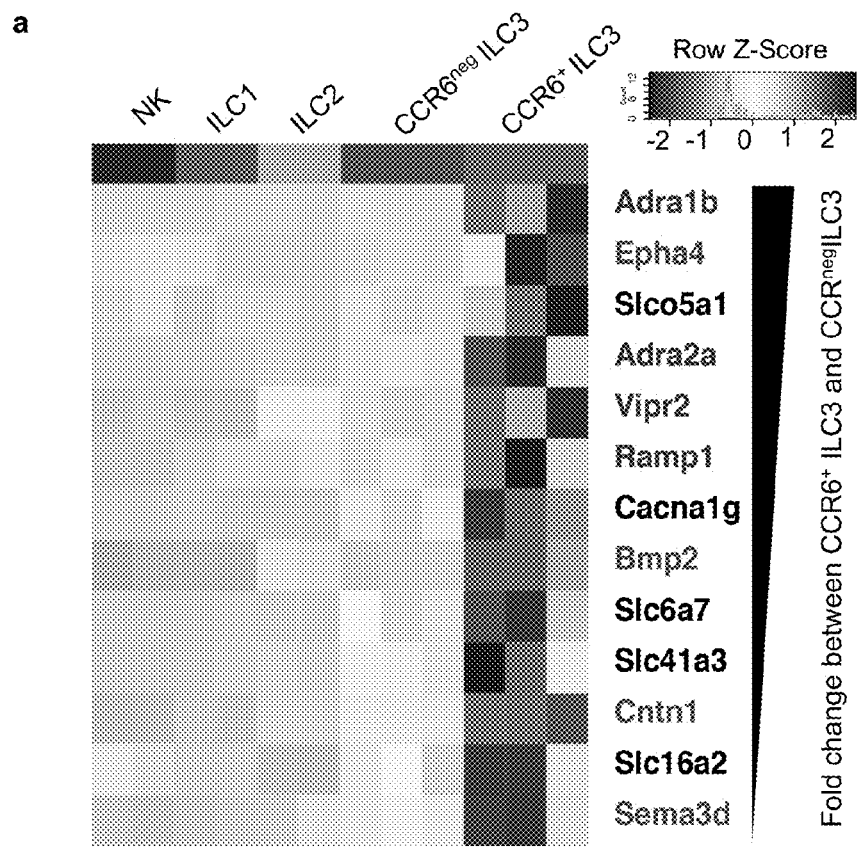
FIG. 1. Processes of VIP-producing enteric neurons are in close proximity to Vipr2-expressing ILC3 within cryptopatches. a, Heatmap of differentially expressed neural-related genes between intestinal CCR6$^+$ LC3 and CCR6$^{neg}$ ILC3 (Fold change ≥2, p-value <0.05, GSE116092). Color scale is based on normalized read counts. Genes are listed on the right hand margin ranked based on the relative fold change, and color coded: Green: Neurotransmitter/neuropeptide receptors, Blue: genes related to nervous system development/axonal guidance and contact. Expression in other ILC subsets is included for comparison. b-d, Representative confocal images from the small intestine of Rorc $(\gamma t)^{EGFP/+}$ mice show clusters of intestinal ILC3 (cryptopatch) in close proximity to enteric neurons in the small intestine lamina propria (see supplementary video 1 and 2). Pan-neuronal marker: β3-tubulin$^+$ (red), ILC3: GFP$^+$ TCRβ$^{neg}$ (green and blue, respectively). n=4 mice, 45 ILC3 clusters. e, f, Neurochemical code of cryptopatch-associated enteric neurons. (e) Representative confocal images from the small intestine of Rorc$(\gamma t)^{EGFP/+}$ mice show cryptopatch-associated enteric neurons are positive for VIP. Neurons: β3-tubulin$^+$ (red), VIP$^+$ (green); ILC3: GFP$^+$ (blue).
Figure 1:
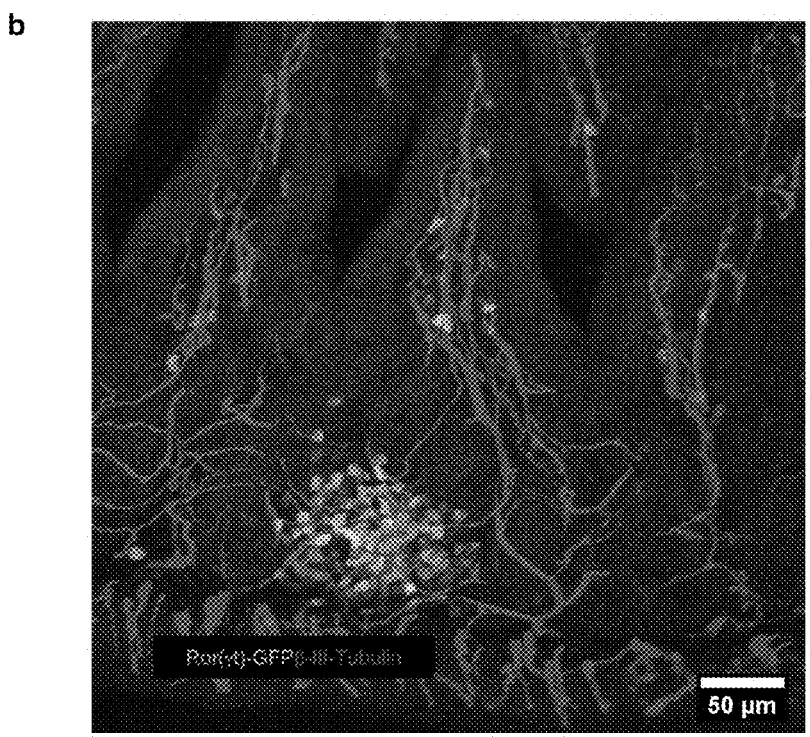
Figure 1:
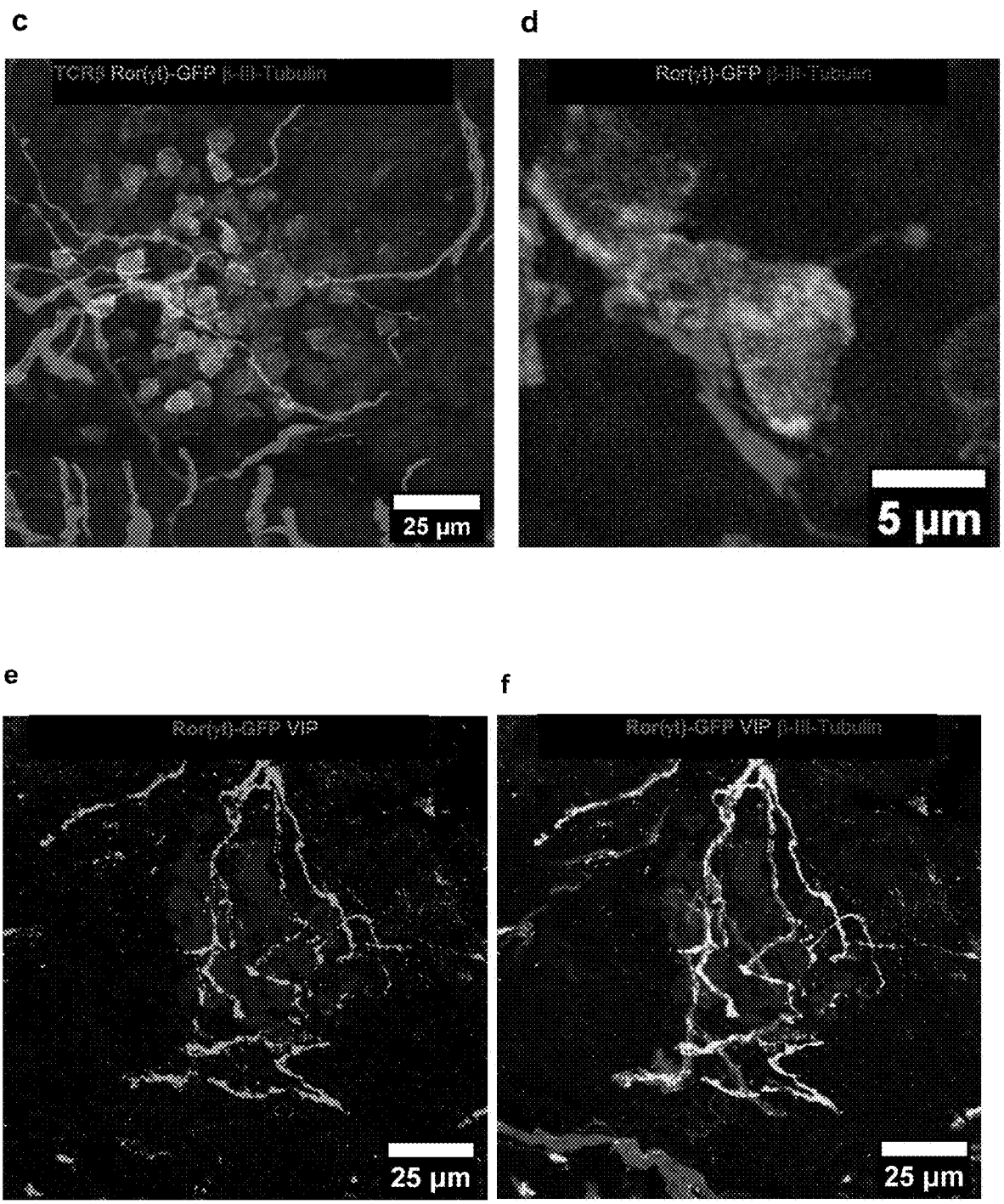

Type 3 innate lymphoid cells (ILC3) promote maintenance of intestinal immune and metabolic homeostasis by integrating cytokine-mediated and glia-derived cues and, through the production of IL-22 and other cytokines, conveying information from the luminal microbiota to intestinal epithelial cells (IECs) and cells in the lamina propria. The activation of ILC3 is regulated by cytokines, including IL-23, IL-1β, and TL1A, which are produced by mononuclear phagocytes and induced by intestinal microbe-derived stimuli. Cytokines produced by activated ILC3, particularly IL-22, support the production of antimicrobial peptides (e.g. RegIIIγ) and mucin by IECs, ensuring spatial segregation of microbes from the intestinal tissue. This microbiota-ILC3-IEC circuit promotes intestinal barrier function by controlling intestinal commensal microbiota and mediating rapid protective responses to enteropathogens. Different subtypes of ILC3s are present within the intestinal lamina propria and are dispersed or in tertiary lymphoid tissue clusters known as cryptopatches (CPs) and isolated lymphoid follicles (ILFs). In perusing transcriptomic datasets of small intestinal ILCs, we identified in CCR6$^+$ ILC3, which comprise the lymphoid tissue inducer (LTi) cells enriched in CPs and ILFs, selective expression of multiple neurotransmitter/neuropeptide receptors and genes related to axonal guidance and neuron differentiation when compared to CCR6$^{neg}$ 9ILC3 and NCR$^+$ ILC3 (FIG. 1a and FIG. 5a-c). This prompted us to evaluate whether CCR6$^+$ ILC3 in the intestinal lamina propria were associated with neuronal projections from the enteric nervous system (ENS). The ENS is part of the peripheral autonomic nervous system, which controls gastrointestinal functions by promoting rapid gut responses to changes in the luminal compartment (e.g. food intake, microbes, metabolites, etc.). We observed that ILC3 in CPs/ILFs were in close proximity to neuronal projections in the lamina propria (FIG. 1b-d). The CP/ILF-associated neuronal projections were positive for vasoactive intestinal peptide upon staining with specific antibody (VIP, FIG. 1e and FIG. 6). We also observed association of VIPen and colonic lymphoid patches (FIG. 7a,b). Indeed, ILC3 in CPs/ILFs were closer to VIP$^+$ enteric neurons (VIPen) than to neurons positive for substance P or tyrosine hydroxylase (which produce norepinephrine or dopamine) (FIG. 1f and FIG. 6). Based on these anatomical findings, together with the fact that CCR6$^+$ ILC3 express a high amount of VIP receptor type 2 (Vipr2) (FIG. 1a), we further investigated whether signaling from VIPen could modulate CCR6$^+$ ILC3 functions and intestinal immune homeostasis.

We isolated ILC3 from the lamina propria of the small intestine of C57BL/6 mice (FIG. 8a) and observed that in vitro activation of VIPR2 inhibited IL-23-induced production of IL-22 by CCR6$^+$ ILC3 (FIG. 2a,b and FIG. 8b,c), although there was no effect on cell activation (marked by Sca-1 up-regulation) or on IL-22 production by CCR6$^{neg}$ 9ILC3 (FIG. 8d-f). In order to investigate the in vivo role of VIPR2 activation in CCR6$^+$ ILC3 functions, we generated mixed bone marrow chimeric mice reconstituted with a 1:1 ratio of isotype-marked Vipr2$^{-/-}$ and Vipr2$^{-/-}$ cells. IL-22 was expressed in a greater proportion of Vipr2$^{-/-}$ CCR6$^+$ ILC3 when compared to Vipr2$^{+/+}$ ILC3 (FIG. 9a,b). We also generated mice with conditional deletion of the gene encoding VIPR2 in ILC3 (Rorc(t)$^{Cre}$Vipr2$^{fl/fl}$, or ILC3$^{\Delta Vipr2}$) and found that a larger proportion and number of CCR6$^+$ ILC3 isolated from the small intestine of ILC3$^{\Delta Vipr2}$ mice expressed IL-22 than cells isolated from WT littermates (FIG. 2c and FIG. 9c-f). Epithelial RegIIIγ mRNA, regulated by IL-22, was considerably higher in IECs from ILC3$^{\Delta Vipr2}$ mice when compared to WT mice (FIG. 2d), indicated that VIPen-derived neuropeptide acts through VIPR2 to inhibit ILC3-mediated innate immune responses.

Figure 2:
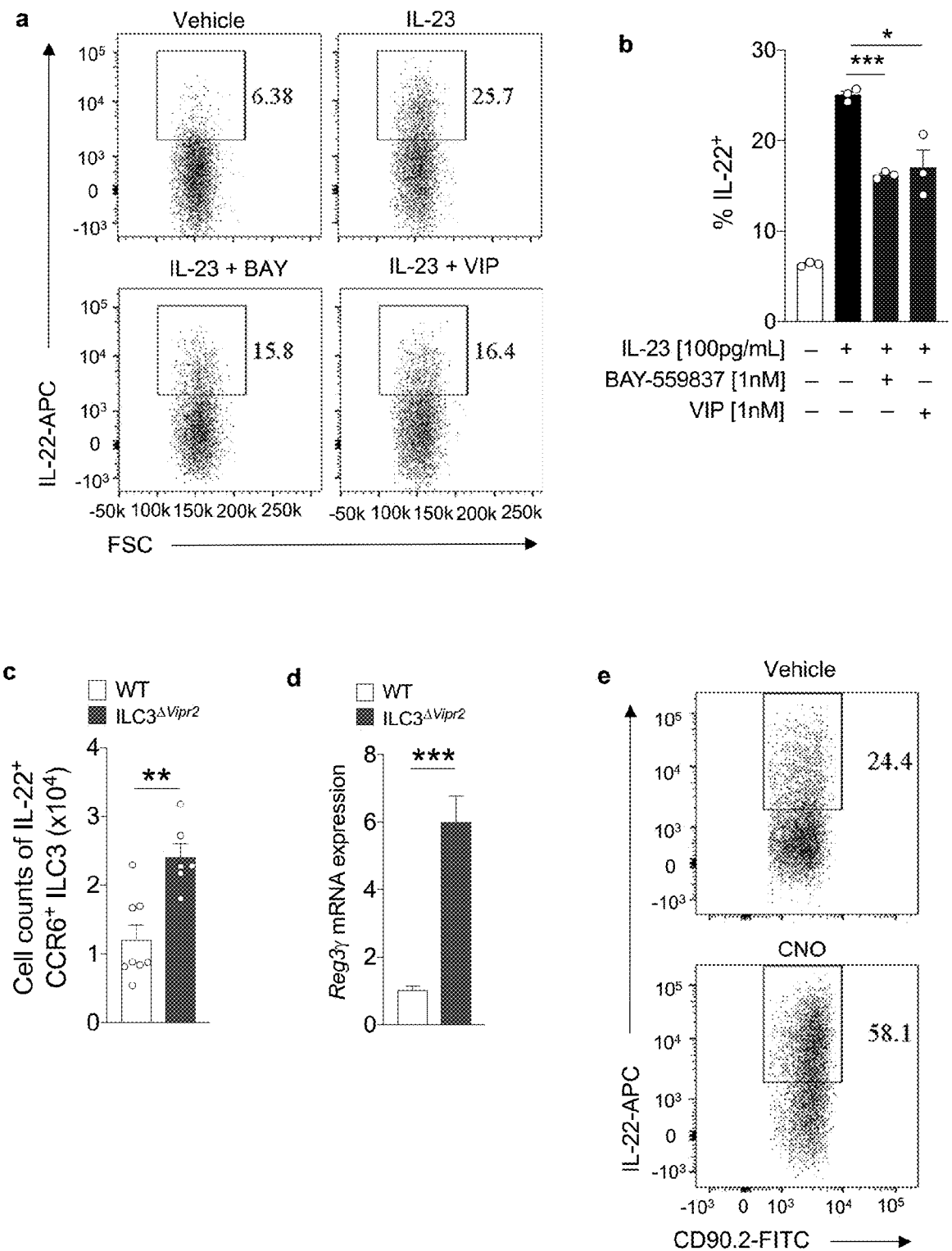
FIG. 2. VIPen promote reduction of mucosal barrier function by VIPR2-dependent inhibition of CCR6$^+$ ILC3. a, b, Representative FACS plot (a) and summaries (b) indicating IL-22 expression in purified CCR6$^+$ ILC3 after in vitro IL-23 stimulation with/without VIPR2 agonist ligands. BAY: BAY-559837, VIP: vasoactive intestinal peptide. *P<0.05 and *P<0.001 (t-test). Data are representative of three independent experiments. c, Number of IL-22$^+$ CCR6$^+$ ILC3 present in the ileum of Rorc$^{Cre}$ (WT) and Rorc$^{Cre}$ Vipr2$^{fl/fl}$(ILC3$^{\Delta Vipr2}$). P<0.1 (t-test), WT: 8; ILC3$^{\Delta Vipr2}$: 6. d, Normalized epithelial Reg3γ mRNA from ileum of WT and ILC3$^{\Delta Vipr2}$ mice. *P<0.001 (t-test), WT: 5; ILC3$^{\Delta Vipr2}$: 5. e-g, Effect of VIPen inhibition on ILC3 and intestinal epithelial cells (IEC). Representative FACS plot (e) and summary (f) indicating IL-22 expression in CCR6$^+$ ILC3 from the ileum of Vip$^{IRES-Cre}$ hM4Di$^{fl-stop-fl/+}$ mice (DREADD for VIPen inhibition) 24 h following treatment with vehicle or CNO (Clozapine-N-oxide, DREADD ligand). Vehicle: n=5, CNO: n=5. P<0.01 (t-test). Data representative of three independent experiments. g, Normalized Reg3γmRNA expression in IEC at 24 h following treatment. Vehicle: n=3, CNO: n=3. *P<0.05 (t-test). Data representative of two independent experiments. h-j, Effect of VIPen activation on ILC3 and IEC. Representative FACS plot (h) and summaries (i) indicating IL-22 expression in CCR6$^+$ ILC3 from ileum of Vip$^{IRES-Cre}$ hM3Dq$^{fl-stop-fl/+}$ (DREADD for VIPen activation) 24 h following the treatment with vehicle or CNO. Vehicle: 6, CNO: 7. **P<0.01 (t-test). j, Normalized epithelial Reg3γ mRNA at 24 h following treatment with vehicle or CNO. Vehicle: 7, CNO: 6. *P<0.05 (t-test). Data representative of three independent experiments. k, l, Dissemination of C. rodentium to the (k) spleen and (l) liver in Vip$^{IRES-Cre}$ hM3Dq$^{fl-stop-fl/+}$ mice treated with vehicle or CNO (1 mg/Kg, daily) for 4 days post-intragastric infection with 2×10$^9$ CFU. Log$_{10}$ Colony Forming Units (CFU) of C. rodentium 9 days post-oral inoculation (9 d.p.i.). Dotted line: limit of detection. *P=0.0009 and **P<0.0001, (Mann-Whitney test).
Figure 2:
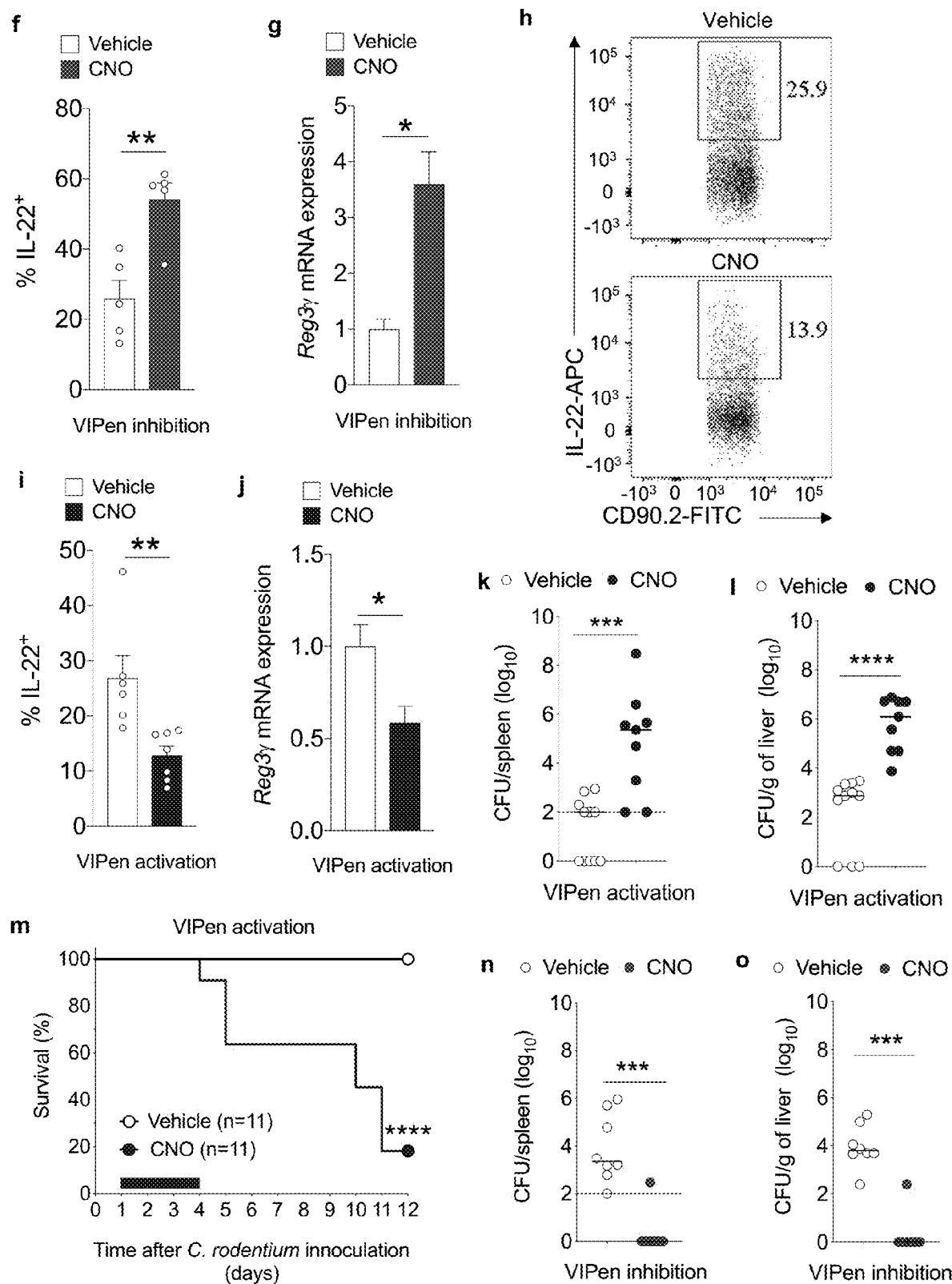

To determine whether direct modulation of VIPen (inhibition or activation) could affect ILC3 function, we adopted a chemogenetic strategy utilizing mice engineered to express designer receptors exclusively activated by designer drugs (DREADD). We selectively expressed inhibitory DREADD (hM4Di) in VIPen of Vip$^{IRES-Cre}$ hM4Di$^{fl-stop-fl/+}$ mice and observed a higher frequency of IL-22-producing CCR6$^+$ ILC3 at 24 h following VIPen inhibition with the DREADD ligand clozapine-N-oxide (CNO, FIG. 2e,f). In parallel, there was increased RegIIIγ mRNA expression in the IECs after VIPen inhibition (FIG. 2g). Conversely, mice expressing the activating DREADD (hM3Dq) in VIPen (Vip$^{IRES-Cre}$hM3Dq$^{fl-stop-fl/+}$ mice) had fewer IL-22$^+$ cells among the CCR6$^+$ ILC3 and lower RegIIIγ mRNA in IECs following VIPen activation with CNO (FIG. 2h-j). Combined, these results indicate that VIPen modulates intestinal immune homeostasis, acting through VIPR2 on CCR6$^+$ ILC3 to inhibit cell activation and IL-22 production.

We next investigated whether alteration of VIPen activity contributes to changes of intestinal barrier function during intestinal colonization with an enteropathogen. Following infection with *Citrobacter rodentium* there was increased Vip mRNA expression in the proximal colon and cecum and of VIP amounts in the portal vein, but not in the peripheral blood (FIG. 10a-c), suggesting an increase in VIPen activity in the intestinal tissue. Oral gavage of mice with a relatively low dose of *C. rodentium* (2×10$^9$ CFU) is tolerated by mice with an intact immune system. However, DREADD-mediated activation of VIPen during the first 4 days of infection led to increased bacterial translocation to the spleen and liver (FIG. 2k,l) and resulted in reduced survival (FIG. 2m), despite only a moderate increase in the amount of luminal *C. rodentium* (Extended Data FIG. 6d). Gavage with a high dose of *C. rodentium* ($4 \times 10^{10}$ CFU) resulted in large amounts of bacteria that translocated to the liver and spleen (9d.p.i.) (FIG. 2n,o). DREADD-mediated inhibition of VIPen provided substantial protection from bacterial breach of the intestinal barrier without affecting the bacterial burden in the feces (FIG. 2n,o and FIG. 10e). Moreover, treatment with recombinant murine IL-22 reversed the effect of DREADD-mediated activation of VIPen on mortality and bacterial translocation (FIG. 10f,g) Activation of VIPen during the events that follow infection with enteropathogens may therefore be an important contributor to intestinal barrier breakdown, which could be mitigated by inhibition of enteric VIP activity on ILC3.

These results indicate the existence of physiological signals that promote activation of VIPen during homeostasis, with consequent tonic inhibition of CCR6$^+$ ILC3. Food ingestion has been reported to rapidly signal VIP release in the intestine (Chayvialle et al., *Gastroenterology.* 1980; 79(5 Pt 1):844-852). We observed a greater amount of VIP in the ileum of mice sampled during the vivarium's dark-phase as compared to the light-phase, which correspond to periods of food consumption and resting, respectively (FIG. 11a). Due to the ad libitum feeding scheme, approximately 15% of daily food intake occurs during the light-phase/resting period (Kohsaka et al., *Cell Metab.* 2007; 6(5):414-421). To dissect the effect of food intake on the VIPen immune inhibitory axis and to reduce the noise created by feeding during the resting period, we restricted food availability for two weeks to alternating 12 h cycles of feeding and fasting. To dissociate the effects of light/dark cycles from time of feeding, food was available to a group of mice only during the dark-phase (night-fed mice, ZT12-ZT0/6 PM-6 AM), while another group had food available only during the light-phase (day-fed mice, ZT0-ZT12/6 AM-6 PM). Using this scheme, we observed more VIP in the portal vein, but not in the peripheral blood, after 6 h of food availability when compared to mice fasted for 6 h, regardless of whether mice were fed during the light phase (ZT 6) or during the dark phase (ZT 18) (FIG. 11b,c). In turn, the frequency of IL-22$^+$ CCR6$^+$ ILC3 was reduced during the periods of food consumption (at 6 h of feeding) relative to fasting periods (fasted for 6 h), independently of light-dark cycles (FIG. 3a,b).

Using the mixed bone marrow chimeric mice, we observed among the Vipr2$^{+/+}$ CCR6$^+$ ILC3 a reduced frequency of IL-22$^+$ cells at 6 h after start of food consumption (ZT 18) when compared to mice fasted for 6 h (ZT 6) (FIGS. 3c and 3d). In contrast, there was no difference in frequency of IL-22$^+$ cells in the Vipr2$^{-/-}$ CCR6$^+$ ILC3 population with or without feeding. This is consistent with VIPR2 signaling-dependent inhibition of IL-22 production in CCR6$^+$ ILC3 following food intake. This conclusion was further supported by the observed reduction in the frequency of IL-22$^+$ CCR6$^+$ ILC3 at 6 h following intragastric delivery of a liquid test diet, but not control saline, during the light-phase period (ZT1-ZT7) (FIG. 3e,f). Furthermore, DREADD-mediated inhibition of VIPen abrogated the effect of the test diet on ILC3 (FIGS. 3e and 3f). These results suggest a fast and dynamic temporal control of intestinal CCR6$^+$ ILC3 function promoted by food intake-mediated activation of VIPen and VIPR2.

Because IL-22 acts on intestinal epithelial cells to regulate barrier functions, including their interactions with commensal microbiota, we next examined whether the neuroimmune inhibitory circuit promoted by food consumption influences host-microbial interactions. Food consumption had a striking effect on the morphology of the ileal epithelium-associated segmented filamentous bacteria (SFB) (FIG. 4a,b, and FIG. 11d,e). SFB attached to IECs had long segmented filaments after 12 h of food consumption, independently of light/dark cycles. However, in the ileum of mice fasted for 12 h, independently of light-cycle, epithelium-associated SFB had few segments and were stubble-like. In ILC3$^{\Delta Vipr2}$ mice, which have increased IL-22 production, SFB failed to form segmented filaments even after 12 h of food consumption (FIG. 4c,d). These results suggest that VIPen regulate growth of the commensal microbiota by activating VIPR2 and modulating cryptopatch-associated ILC3 in response to food consumption.

We examined the role of the VIPen-ILC3-IL-22 circuit in lipid absorption. Mice were adapted for 2 weeks to 12 h restricted feeding during light or dark cycles and were then gavaged with $^3$H-triolein following feeding or fasting. Mice that had been fed for 12 h absorbed more of the triglyceride than mice fasted for 12 h, although there was some effect of circadian regulation (light/dark adaptation) (FIG. 11f,g).

The effect of food intake on lipid absorption was dependent on VIPen inhibition of ILC3, since expression of lipid transporter mRNAs, $^3$H-triolein absorption, and concentrations of circulating plasma triglycerides were substantially reduced in ILC3$^{\Delta Vipr2}$ when compared to WT mice after 12 h of feeding (ZT 0) (FIGS. 4e-g). Finally, continuous intragastric delivery of a liquid test diet for 6 h during the light phase period led to an increase in serum triglycerides, which was blocked by DREADD-mediated inhibition of VIPen (FIG. 4h).

These results reveal an important neuro-immune circuit in which activation of VIPen antagonize microbiota-dependent CCR6$^+$ ILC3 function, resulting in reduced IL-22 production and increased efficiency of lipid absorption. The benefit of greater nutrient acquisition comes at the expense of reduced barrier function, illustrated by susceptibility to enteropathic bacteria and rapid growth of epithelial-associated commensal SFB. Whether the host derives benefit from the reduced anti-microbial activity is unclear, although it may enable bacteria-dependent generation of essential metabolites and vitamins that would be readily absorbed.

Our results indicate that activation of VIPen and VIPR2 could reduce intestinal barrier functions and promote dysbiosis and at the same time contribute to metabolic imbalance. Moreover, enteropathogens may hijack this neuro-immune circuit and reduce intestinal barrier functions, facilitating intestinal colonization. In these scenarios, VIPR2 inhibitors may be valuable therapeutic tools to reduce lipid absorption or enforce the barrier during acute gastrointestinal infections.

Methods

Mice

C57Bl/6 mice were obtained from Taconic Farm. All transgenic mice were bred and maintained in the animal facility of the Skirball Institute (New York University School of Medicine) in specific pathogen-free conditions. hM3Dq$^{fl-stop-fl}$ mice (CAG-LSL-Gq-DREADD, Jax #026220), hM4Di$^{fl-stop-fl}$ mice (CAG-LSL-Gi-DREADD, Jax #026219), VIP$^{IRES-Cre}$ mice (B6J.Vip-IRES-Cre, Jax #031628) and CD45.1 mice (B6.SJL-Ptprca Pepcb/BoyJ, Jax #002014) were purchased from Jackson Laboratories. Rorc(γt)$^{EGFP/+}$ and Rorc$^{Cre}$ mice were generated in our laboratory and previously described (Eberl et al., *Nat Immunol.* 2004; 5(1):64-73; Margolis et al., *Trends Neurosci.* 2016; 39(9):614-624). Vipr2$^{-/-}$ mice (Jax #031332) were purchased from Jackson Laboratories and were maintained in a CD45.2 background or were bred with CD45.1 (B6SJL-Ptprca Pepcb/BoyJ) mice, which subsequently generated Vipr2$^{-/-}$ CD45.1/2 mice and WT CD45.1 littermates. Conditional VIPR2 knockout (Vipr2fl) mice were generated using CRISPR-Cas9 technology as described below. Mice in all experiments were 6-12 weeks old at the starting point of treatments and all were colonized with SFB. All animal procedures were performed in accordance with protocols approved by the Institutional Animal Care and Usage Committee of New York University School of Medicine or the NIAID as applicable.

Generation of ILC3$^{\Delta Vipr2}$ Mice

Mice carrying loxP sites flanking exons 3 and 4 of the Vipr2 gene (Vipr2$^{fl/fl}$) were generated using published CRISPR/Cas9 protocols (Wang et al., *Cell.* 2013; 153(4): 910-918; Yang et al., *Nat Protoc.* 2014; 9(8):1956-1968) at the NYU School of Medicine's Rodent Genetic Engineering Laboratory. Briefly, guide RNAs targeting regions upstream of exon 3 (gRNA_16 sequence: GAAATCTCACAACA-GATTCG—SEQ ID NO:1) and downstream of exon 4 (gRNA_23 sequence: TCTCCTCAGAAGCATCGAAT—SEQ ID NO:2) were designed using the Crispr guide design software (crispr.mit.edu). gRNA recognition sequences were cloned into the pX330 vector (a gift from Dr. Feng Zhang, Addgene #42230), using oligos with a T7 promoter containing the gRNA template that were chemically synthesized by IDT (Integrated DNA Technologies). The products of PCR-amplified T7-gRNA were used as templates for in vitro transcription (MEGAshortscript T7 kit, Thermo Fisher Scientific). The gRNAs were purified using the MEGAClear Transcription Clean-up kit (Thermo Fisher Scientific). Two donor templates (ssDNA_1 and ssDNA_2) with 200 bp each were chemically synthesized by IDT. The donor templates contained 60 bp homology arms flanking a cassette containing a loxP sequence and XhoI or SalI restriction sites, located in the original PAM sequence (mutated PAM). Namely, ssDNA_1 (XhoI) for the region upstream exon 3: (GGATGGCATTTACATAGGACCC-CATCCCAGTGGCTGCTCAGAAGAGCACTCACTCCT TATCCctcgagataacttcgtataatgtatgctatacgaagt-tatCCGAATCTGTTGTGAGATTTCGAGAACTCA TAAGGACTGATAAGGCCACACAACTTGAGCXSEQ ID NO:3), and ssDNA_2 for the region downstream exon 4 (TGATTTCTCCTAGGTCACACTCAGGGAGCAT-TTCCAGACACTGGAAAACTCCTGAGG CCCgtcgacat-aacttcgtataatgtatgctatacgaagttatATTCGATGCTTCTGAG-GAGACTATAATTAAAC CCTGCCTGTGTGAGGCATGGCTTCTGAT) (SEQ ID NO:4). Mice were generated by injection of a mixture of mammalian optimized Cas9 mRNA (100 ng/μl, TriLink Biotechnologies), purified gRNA_16 and gRNA_23 (50 ng/μl, each) and donor templates ssDNA_1 and ssDNA_2 (50 ng/ul, each) in injection buffer (10 mM Tris, pH 7.5; 0.1 mM EDTA) into the cytoplasm of C57BL/6J embryos in accordance with standard procedures approved by the IACUC at the NYU School of Medicine. Female CD-1 mice (Charles River) were used as foster mothers. F0 mice were genotyped and sequenced (Sanger sequencing) to identify mice homozygous for both loxP insertions. Founders bearing loxP insertions were then backcrossed at least one time to wild-type C57BL/6J mice generating the Vipr2$^{fl/fl}$ mice. For the generation of ILC3$^{\Delta Vipr2}$ mice, Vipr2$^{fl/fl}$ mice were crossed with Rorc$^{Cre}$ mice for the generation of Rorc$^{Cre}$ Vipr2$^{fl/fl}$ and Rorc$^{Cre}$ Vipr2$^{+/+}$ littermates.

VIPen Activation/Inhibition Using DREADDs

To perform chemogenetic activation or inhibition of VIPen, we bred VIP$^{IRES\text{-}Cre}$ homozygous mice to hM3Dq$^{fl\text{-}stop\text{-}fl}$ mice (DREADD for activation) or hM4Di$^{fl\text{-}stop\text{-}fl}$ bp-mice (DREADD for inhibition), generating VIP$^{IRES\text{-}Cre}$ hM3Dq$^{fl\text{-}stop\text{-}fl}$ (VIPen activation) and VIP$^{IRES\text{-}Cre}$ hM3Dq$^{fl\text{-}stop\text{-}fl}$hM4Di$^{fl\text{-}stop\text{-}fl}$ mice (VIPen inhibition). To perform 24 h activation of the DREADDs, mice were treated with Clozapine-N-Oxide (CNO, 1 mg/Kg intraperitoneally, TOCRIS) each 12 h. Our pilot experiments in C57BL/6 mice (data not shown) revealed that at these dose CNO treatment does not affect ILC3 function. To perform activation of the DREADDs during *Citrobacter rodentium* infection, mice were treated daily with CNO (1 mg/Kg, intraperitoneally) from day 1 to day 4 after infection.

Food Restriction Protocol

For a period of two weeks, food was made available to mice only for 12 h per daily cycle. Mice were kept in two different regimens: Dark-phase fed mice, with food being available between 6 PM-6 AM (ZT 12→ZT 0); and light-phase fed, with food being available between 6 AM-6 PM (ZT 0→ZT 12). To avoid littering, at the beginning of the fasting period of each regimen, mice were transferred to a clean cage containing alpha cellulose clean bedding (Shepherd's™ ALPHA-dri). Mice were provided with free access to water.

Gavage of Liquid Test Diet

Dry powder micro stabilized rodent liquid diet (Test Diet, LD 101) was blended (mechanical blender) vigorously for 30 seconds in saline (NaCl 0.9%) at 0.5 g/mL. Mice were gavaged with 400 ul of this solution using a polyurethane feeding tube (16ga×38 mm, FTPU-16-38-50, INSTECH) every 45 min for 6 h.

Generation of Bone Marrow VIPR2$^{+/+}$/VIPR2$^{-/-}$ Chimeric Reconstituted Mice Bone marrow mononuclear cells were isolated from CD45.1 VIPR2$^{+/+}$ and CD45.2 (or CD45.1/2) VIPR2$^{-/-}$ mice by flushing the long bones. Red blood cells were lysed with ACK Lysing Buffer and the remaining cells were resuspended in PBS for injection in at a 1:1 ratio (WT: VIPR2 KO). 4×10$^6$ cells were injected intravenously into 6 week old CD45.1/2 (CD45.2) mice that were irradiated 4 h before reconstitution using 1000 rads/mouse (2×500 rads, at an interval of 3 h, at X-RAD 320 X-Ray Irradiator). To deplete intestinal ILC3, one day after the bone marrow transfer, mice were treated with InVivoMAb anti-mouse Thy1.2 (200 ug/mice for 4 consecutive days, Clone 30H12, BioXCell). Experiments were performed 6-7 weeks after the last treatment with α-Thy1.2.

Radioactively Labeled Triglyceride Absorption Assay

Plasma $^3$H-CPM (counts per minute) was measured 1-4 h after gavage with $^3$H-Triolein-containing lipid (Zhang et al., *Science.* 2018; 361(6402):599-603). Briefly, mice were injected with poloxamer 407 (1 g/Kg, i.p., Sigma, #16758). After 30 minutes, mice were gavaged with a mixture of 2 μCi 3H-Triolein in 200 ul of 20% intralipid oil emulsion. Blood samples were collected and diluted in Liquid Scintillation Counting cocktail (Ultima Gold) and measured using a Scintillation counter (Beta Counter MicroBeta$^2$ System, Perkin Elmer).

*C. rodentium* Mediated Colon Inflammation

*C. rodentium* strain DBS100 (ATCC51459; American Type Culture Collection) was grown at 37° C. in LB broth to OD600 reading between 0.5 and 0.7. VIP$^{IRES\text{-}Cre}$hM3Dq$^{fl\text{-}stop\text{-}fl}$ (VIPen activation) and C57BL/6 mice were inoculated with 200 μl of a bacterial suspension (2×10$^9$ CFU) by oral gavage. VIP$^{IRES-Cre}$ hM3Dq$^{fl-stop-fl}$hM4Di$^{fl-stop-fl}$ mice (VIPen inhibition) were inoculated with 200 μl of a bacterial suspension (4×10$^{10}$ CFU) by oral gavage. For DREADD experiments, CNO treatment started at 1 day post-infection (d.p.i.) until 4 d.p.i. Mice were followed the next 12 days post-infection (d.p.i.) to measure survival rate. At 9 d.p.i. fecal pellets were collected and the mice dissected to harvest spleen and liver. Samples were weighted and minced on sterile deionized water with Triton 0.1% and filtered on a 70 μm cell strainer. The filtered samples were used to measure *C. rodentium* burden with serial dilutions (triplicates) on MacConkey agar plates.

Immunofluorescence and Confocal Microscopy

Small intestine from SFB$^+$ Rorc(γt)$^{EGFP/+}$ mice were Swiss-rolled, fixed for 4 h in 4% paraformaldehyde, incubated overnight in 30% sucrose at 4° C., and frozen in embedding medium for frozen specimens (O.C.T, Tissue-Tek, Sakura). Tissue was cut into 30-70 μM sections, blocked in PBST 0.5% (0.5% Triton X-100, 10% normal donkey serum) for 1 h, and incubated overnight using a combination of 3 of the following antibodies for 1 h: α-Vasoactive Intestinal Peptide (1:1000, rabbit polyclonal, 20077, Immunostar), α-Tyrosine Hydroxilase (1:50, rabbit polyclonal, AB152, Millipore), α-Substance P (1:3000, rabbit polyclonal, 20064 Immunostar), α-GFP Alexa Fluor 488 (1:500, clone: FM264G, Biolegend), α-TCRβ Brilliant Violet 421 (1:50, Biolegend), α-β-3-Tubulin Alexa Fluor 594 (1:500, clone:AA10, Biolegend). Tissue was washed and when needed incubated with secondary fluorescently labeled antibodies (Donkey Anti-Rabbit Pacific Blue or Alexa Fluor 647) for 2 h before nuclear staining with Draq-7 (R&D Systems) or 4',6-diamidino-2-phenylindole (DAPI, ThermoFisher). Images were acquired using a Zeiss LSM 710 confocal (Carl Zeiss). The imaging data were processed and analyzed using Image J software (NIH, Bethesda, MD). Imaris software version 9.0.1 (Bitplane; Oxford Instruments) was used to generated reconstructed 3D images.

Isolation of Lamina Propria Lymphocytes (LPLs) from the Small Intestine

Whole small intestine or the ileum (distal 14 cm of the small intestine) was dissected from mice. Mesenteric fat tissue and Peyer's patches were carefully removed from these tissues. Intestinal tissue was opened and extensively cleaned of fecal matter. Following, this tissue was sequentially treated with HBSS 1× (1 mM DTT) at 37° C. for 10 min with gentle shaking (200 rpm), and twice with 5 mM EDTA at 37° C. for 10 min to remove epithelial cells. The EDTA fraction (epithelial cell-enriched) was filtered, centrifuged and suspended in Trizol for further RNA isolation. The remaining tissue was then minced with a scissor and dissociated in RPMI containing 10% FBS, Dispase (0.05 U/ml; Worthington), collagenase (1 mg/ml collagenase II; Roche) and DNase I (100 μg/ml; Sigma) at constant shaking at 37° C. for 45 min (175 rpm). The digested tissue was then filtered through a 70 μm strainer to remove large debris. Viable Lamina Propria Lymphocytes (LPLs) were collected at the interface of a 40%/80% Percoll/RPMI gradient (GE Healthcare).

ILC3 In Vitro Cell Culture

CCR6$^+$ and CCR6$^{neg}$ ILC3 (DAPI$^{neg}$CD3$^{neg}$CD11c$^{neg}$CD14$^{neg}$CD19$^{neg}$TCRβ$^{neg}$ TCRγ$^{neg}$NK1.19KLRG1$^{neg}$CD127$^+$CD90.2$^+$) were isolated from small intestine LPLs of C57BL/6 mice using the ARIA II FACS Sorter (BD Biosciences). ILC3 were cultured at 37° C. in flat bottom 96 well plates (10$^4$ cells/well) in RPMI supplemented with 10% heat-inactivated FBS (Hyclone), 50 U penicillin-streptomycin (Hyclone), 2 mM glutamine (Hyclone), 10 mM HEPES (Hyclone), 1 mM sodium pyruvate (Hyclone) and 50 μM β-mercaptoethanol (Gibco). ILC3 were stimulated with IL-23 (100 pg/mL, R&D systems) and/or VIPR2 ligands (BAY-559837: 1-100 nM, and VIP: 1 nM, TOCRIS) for 16 h (37° C.), washed, incubated in complete media in the presence of Golgi Plug (BD Bioscience) for 4 h (37° C.), and stained for membrane extracellular markers in Staining Buffer (PBS FBS2% EDTA 5 mM) and for intracellular markers using Cytofix/Cytoperm buffer set following manufacturer's protocol (BD Biosciences). Acquisition of cytometric parameters was performed on an LSRII (BD Biosciences). All data were analyzed using FlowJo Software Version 10 (Tree Star).

Antibodies for Intracellular Staining and Flow Cytometry

Live/dead fixable blue (ThermoFisher) or DAPI (ThermoFisher) were used to exclude dead cells. The following monoclonal antibodies were purchased from eBiosciences, BD Pharmingen or BioLegend: CD3, CD45.1, CD45.2, TCRβ, CD11c, CD14, CD19, TCRβ, TCRγ, NK1.1, CD127, CD90.2, CCR6, Sca-1 and IL-22. For cytokine analysis, cells were incubated for 4 hours at 37 C in RPMI with 10% FBS and GolgiPlug (BD). Cells were stained for surface markers before fixation and permeabilization, and then subjected to intracellular cytokine staining for IL-22 according to the manufacturer's protocol (Cytofix/Cytoperm buffer set from BD Biosciences). Flow cytometric analysis was performed on an LSR II (BD Biosciences) or an Aria II (BD Biosciences) and analyzed using FlowJo software version 10 (Tree Star).

Blood Collection

Peripheral and portal vein blood were collected under general anesthesia (Ketamine 100 mg/Kg, Xylazine 15 mg/Kg). Peripheral blood was collected through orbital venous plexus bleeding with a glass capillary in a tube containing EDTA (25 mM) as an anticoagulant. Plasma was collected after centrifugation of the collected sample and frozen until processing. Surgery was performed to collect blood from the portal vein, which drains the gastrointestinal tract. Briefly, after laparotomy, the portal vein was localized and the blood was collected with a syringe. Portal vein blood was processed following the same protocol above for peripheral blood.

Tissue Processing for ELISA

Distal Ileum (6 cm from the ileal-cecal junction) or the Large intestine (Cecum+3 cm of the proximal colon) were collected and extensively washed to clean out fecal matter. The samples were weighed and, using a tissue homogenizer, extracted in PBS Tween 0.1% (with protease inhibitor) and centrifuged to remove tissue debris. The supernatant was frozen until measurement of VIP concentrations in the tissue.

EISA for Vasoactive Intestinal Peptide

VIP content was measured in the blood plasma or homogenized tissue following manufacturer's recommendations (EIAM-VIP-1, RayBiotech).

Measurement of Plasma Concentration of Triglycerides

Peripheral blood was collected as described above and plasma was used to quantify triglyceride concentrations following manufacturer's recommendations (Sigma-Aldrich, MAK266).

Scanning Electron Microscopy

Scanning Electron Microscopy was performed on 1-1.5 cm pieces from terminal ileum (2 cm above the ileal-cecal junction). Intestine was cut open and washed to remove fecal matter, pinned in dental wax and fixed for 2 h with a 0.1M sodium cacodylate buffer (CB, pH 7.4) containing 2.5% glutaraldehyde and 2% paraformaldehyde. Samples were post fixed in 1% OsO4 for 2 hours, dehydrated in ethanol, and critical point dried using Tousimis autosamdsri 931 (Rockville, MD). The dried intestines were put on SEM stabs, sputter coated with gold/palladium by DESK V TSC HP Denton Vacuum (Moorestown, NJ), and images were taken on random locations in the tissue by Zeiss Gemini300 FESEM using secondary electron mode at 5 kv. For quantification of SFB length, random fields were selected for measurement using Image J.

RNA Extraction from Intestinal Epithelial Cells and RT-qPCR

TRNA isolation of ileal epithelial cells was performed using TRIzol following manufacturer's instructions (Invitrogen) followed by DNase I (Qiagen) treatment and cleanup with RNeasy MinElute kit (Qiagen) following manufacturer protocols. cDNA was generated using SuperScript™ IV First-Strand Synthesis System (ThermoFisher). Gene-specific primers spanning exons were used: Rps17 (F:'5-cgc-cattatccccagcaag-3' (SEQ ID NO:5))/R:'5-tgtcgggatccacct-caatg-3')(SEQ ID NO:6), RegIIIγ(F:'5-tctgcaagacagacaagatgct-3'(SEQ ID NO:7)/R:'5-ggggcatctttcttggcaac-3'(SEQ ID NO:8)), Fabp2 (F:'5-gtctagcagacggaacggag-3'(SEQ ID NO:9)/R:'5-ctccttcatatgtgtaggtctgga-3')(SEQ ID NO:10), Cd36 (F:'5-tggccttacttgggattgg-3' (SEQ ID NO:11)/R:'5-ccagtgtatatgtaggctcatcca-3'(SEQ ID NO:12)). Quantitative PCR was performed using the Hot Start-IT SYBRGreen (Affymetrix) on the Roche real-time PCR system (Roche 480). Values were normalized to Rps17 gene for each sample.

Data Processing of Public Available RNA-Seq

DESeq2-normalized gene quantification and differential expression analysis were downloaded from GSE116092 (Pokrovskii et al., *Immunity*. 2019). Raw counts were downloaded from GSE127267 (ImmGen ULI RNA-seq data) (Heng et al., *Nat Immunol*. 2008; 9(10):1091-1094) and differential expression analysis was performed using DESeq2. Normalized counts were used for downstream analysis. A cutoff was made based on the normalized counts of a non-expressed gene (Foxp3) (GSE116092, cut-off ≤9 and for GSE127267, cut off <25). A list with neural-associated related genes list was made from 3 databases—KEGG, Amigo2, and G3Cdb. For the KEGG list, all genes involved in the following pathways were included: Glutamatergic synapse, GABAergic synapse, Cholinergic synapse, Dopaminergic synapse, Serotonergic synapse, Long-term potentiation, Long-term depression, Retrograde endocannabinoid signaling, Synaptic vesicle cycle, Neurotrophin signaling pathway, Axon guidance, Circadian rhythm, Circadian entrainment, Neuroactive ligand-receptor interaction, Cell adhesion molecules (CAMs), and cAMP signaling pathway. The Amigo2 list included genes from the following GO classes—vasoactive intestinal polypeptide receptor activity, G protein-coupled peptide receptor activity, nervous system development, positive regulation of neuron projection development, cerebellum development, neuron projection development, anchored component of postsynaptic membrane, and anchored component of pre-synaptic membrane. The G2Cdb list was formed with genes from the following lists—L00000001, L00000008, L00000060, L00000062, L00000070 and L00000072. GO term analysis of GSE116092 was done using g:Profiler. For heat maps, genes were considered differentially expressed with FDR<0.01 and log 2 fold change ≥2.

Statistical Analysis

Unpaired two-sided t-test, paired two-sided t-test, one-way ANOVA with multiple comparisons with Bonferroni correction, two-way ANOVA with multiple comparisons and Bonferroni correction, Mann-Whitney test, Mantel Cox test (for survival curves), were performed to compare the results using GraphPad Software Version 8 (GraphPad Software). No samples were excluded from analysis. We treated less than 0.05 p value as significant. *P<0.05,  P<0.01, * P<0.001, and **** P<0.0001. Details regarding number of replicates and the definition of center/error bars can be found in figure legends.

While the present invention has been described through illustrative embodiments, routine modification will be apparent to those skilled in the art and such modifications are intended to be within the scope of this disclosure.

What is claimed is:

1. A method comprising administering to an individual who has inflammatory bowel disease that is due to a microbial infection a composition consisting of an effective amount of an inhibitor of VIPR2 expression or function to thereby reduce severity of the inflammatory bowel disease.

2. The method of claim 1, wherein the inhibitor of VIPR2 activation is VIP(6-28) or [D-p-Cl-Phe$^6$,Leu$^{17}$]-VIP.

3. The method of claim 1, wherein the inhibitor of VIPR2 inhibits binding of VIP to VIPR2.

\* \* \* \* \*

SEQUENCE LISTING

<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: gRNA

<400> SEQUENCE: 1
gaaatctcac aacagattcg                    20

<210> SEQ ID NO 2
<211> LENGTH: 20
<212> TYPE: DNA
<213> ORGANISM: Artificial Sequence
<220> FEATURE:
<223> OTHER INFORMATION: gRNA

<400> SEQUENCE: 2
tctcctcaga agcatcgaat                    20

```
<210> SEQ ID NO 3
<211> LENGTH: 162
<212> TYPE: DNA
<213> ORGANISM: Artificial Sequence
<220> FEATURE:
<223> OTHER INFORMATION: ssDNA_1

<400> SEQUENCE: 3
ggatggcatt tacataggac cccatcccag tggctgctca gaagagcact cactccttat      60
ccctcgagat aacttcgtat aatgtatgct atacgaagtt atccgaatct gttgtgagat     120
ttcgagaact cataaggact gataaggcca cacaacttga gc                        162

<210> SEQ ID NO 4
<211> LENGTH: 160
<212> TYPE: DNA
<213> ORGANISM: Artificial Sequence
<220> FEATURE:
<223> OTHER INFORMATION: ssDNA_2

<400> SEQUENCE: 4
tgatttctcc taggtcacac tcagggagca tttccagaca ctggaaaact cctgaggccc      60
gtcgacataa cttcgtataa tgtatgctat acgaagttat attcgatgct tctgaggaga     120
ctataattaa accctgcctg tgtgaggcat ggcttctgat                           160

<210> SEQ ID NO 5
<211> LENGTH: 19
<212> TYPE: DNA
<213> ORGANISM: Artificial Sequence
<220> FEATURE:
<223> OTHER INFORMATION: primer

<400> SEQUENCE: 5
cgccattatc cccagcaag                                                   19

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
tgtcgggatc cacctcaatg                                                  20

<210> SEQ ID NO 7
<211> LENGTH: 22
<212> TYPE: DNA
<213> ORGANISM: Artificial Sequence
<220> FEATURE:
<223> OTHER INFORMATION: primer

<400> SEQUENCE: 7
tctgcaagac agacaagatg ct                                               22

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
ggggcatctt tcttggcaac                                                  20
```

```
<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
gtctagcaga cggaacggag                                           20

<210> SEQ ID NO 10
<211> LENGTH: 24
<212> TYPE: DNA
<213> ORGANISM: Artificial Sequence
<220> FEATURE:
<223> OTHER INFORMATION: primer

<400> SEQUENCE: 10
ctccttcata tgtgtaggtc tgga                                      24

<210> SEQ ID NO 11
<211> LENGTH: 19
<212> TYPE: DNA
<213> ORGANISM: Artificial Sequence
<220> FEATURE:
<223> OTHER INFORMATION: primer

<400> SEQUENCE: 11
tggccttact tgggattgg                                            19

<210> SEQ ID NO 12
<211> LENGTH: 24
<212> TYPE: DNA
<213> ORGANISM: Artificial Sequence
<220> FEATURE:
<223> OTHER INFORMATION: primer

<400> SEQUENCE: 12
ccagtgtata tgtaggctca tcca                                      24
```